United States Patent US 12,342,920 B2
Pan et al. (45) Date of Patent: Jul. 1, 2025

(12) United States Patent
Pan et al.

(10) Patent No.: US 12,342,920 B2
(45) Date of Patent: Jul. 1, 2025

(54) DEPILATOR

(71) Applicant: SHENZHEN ULIKE SMART ELECTRONICS CO., LTD, Guangdong (CN)

(72) Inventors: Yuping Pan, Guangdong (CN); Xiang Li, Guangdong (CN)

(73) Assignee: SHENZHEN ULIKE SMART ELECTRONICS CO., LTD, Shenzhen (CN)

(*) Notice: Subject to any disclaimer, the term of this patent is extended or adjusted under 35 U.S.C. 154(b) by 886 days.

(21) Appl. No.: 17/200,022

(22) Filed: Mar. 12, 2021

(65) Prior Publication Data
US 2021/0393014 A1 Dec. 23, 2021

(30) Foreign Application Priority Data

Jun. 19, 2020 (CN) .................. 202010570807.4
Sep. 29, 2020 (WO) ............... PCT/CN2020/118788
(Continued)

(51) Int. Cl.
*A45D 26/00* (2006.01)
*A61N 5/06* (2006.01)
(Continued)

(52) U.S. Cl.
CPC ....... *A45D 26/0061* (2013.01); *A61N 5/0617* (2013.01); *H05K 7/2039* (2013.01);
(Continued)

(58) Field of Classification Search
CPC .. A45D 26/0023–0061; A45D 2200/15; A45D 2200/155; H05K 7/20; H05K 7/2039; H10N 10/13; A61B 2018/00476
See application file for complete search history.

(56) References Cited

U.S. PATENT DOCUMENTS

2012/0165682 A1   6/2012   Keeney et al.
2013/0160977 A1   6/2013   Fan
(Continued)

FOREIGN PATENT DOCUMENTS

CN   2608928 Y   3/2004
CN   1895011 A   1/2007
(Continued)

OTHER PUBLICATIONS

The International Search Report issued in corresponding International Application No. PCT/CN2020/118788, mailed Mar. 2, 2021, pp. 1-4, Beijing, China.
(Continued)

*Primary Examiner* — Todd J Scherbel

(57) ABSTRACT

The present disclosure discloses a depilator including a cold compressing portion, a heat sink assembly and a heat conducting plate which are located away from the cold compressing portion. The heat conducting plate includes a main heat absorbing portion and a heat outputting portion. The main heat absorbing portion is in contact with the cold compressing portion, to absorb heat of the cold compressing portion. The heat outputting portion is in contact with the heat sink assembly, to conduct the heat to the heat sink assembly. The depilator defines a cooling channel. The depilator comprises a housing; the housing defines at least one cooling inlet and at least one cooling outlet; the cooling channel is formed between the at least one cooling inlet and the at least one cooling outlet; the heat of the heat sink assembly is dissipated through the cooling channel and the at least one cooling outlet.

23 Claims, 16 Drawing Sheets

(30) Foreign Application Priority Data

Oct. 21, 2020 (CN) .......................... 202011134930.8
Oct. 29, 2020 (WO) ................ PCT/CN2020/124733

(51) Int. Cl.
*H01L 35/30* (2006.01)
*H05K 7/20* (2006.01)
*H10N 10/13* (2023.01)
*A61N 5/00* (2006.01)

(52) U.S. Cl.
CPC ......... *H10N 10/13* (2023.02); *A45D 2200/15* (2013.01); *A61N 2005/005* (2013.01); *A61N 2005/0632* (2013.01); *A61N 2005/0644* (2013.01)

(56) References Cited

U.S. PATENT DOCUMENTS

| | | | |
|---|---|---|---|
| 2015/0196271 A1 | 7/2015 | Nair | |
| 2016/0270951 A1 | 9/2016 | Martins et al. | |
| 2019/0175394 A1 | 6/2019 | Kim | |
| 2022/0346871 A1* | 11/2022 | Duan | A61B 18/18 |

FOREIGN PATENT DOCUMENTS

| | | |
|---|---|---|
| CN | 101025344 A | 8/2007 |
| CN | 201403273 Y | 2/2010 |
| CN | 201407936 Y | 2/2010 |
| CN | 105126260 A | 12/2015 |
| CN | 106232014 A | 12/2016 |
| CN | 206294058 U | 6/2017 |
| CN | 207804371 U | 9/2018 |
| CN | 207804372 U | 9/2018 |
| CN | 207980186 U | 10/2018 |
| CN | 208114942 U | 11/2018 |
| CN | 208426208 U | 1/2019 |
| CN | 209316830 U | 8/2019 |
| CN | 209464502 U | 10/2019 |
| CN | 110461281 A | 11/2019 |
| CN | 209572304 U | 11/2019 |
| CN | 209790005 U | 12/2019 |
| CN | 210184830 U | 3/2020 |
| CN | 210331379 U | 4/2020 |
| CN | 210542906 U | 5/2020 |
| CN | 111685869 A | 9/2020 |
| CN | 111700725 A | 9/2020 |
| CN | 211433284 U | 9/2020 |
| CN | 211534779 U | 9/2020 |
| CN | 111743622 A | 10/2020 |
| CN | 211674531 U | 10/2020 |
| CN | 306092557 S | 10/2020 |
| CN | 112057164 A | 12/2020 |
| CN | 112155726 A | 1/2021 |
| CN | 212308032 U | 1/2021 |
| CN | 212326718 U | 1/2021 |
| CN | 214908023 U | 11/2021 |
| EP | 3263177 B1 | 6/2019 |
| ES | 2745124 T3 | 2/2020 |
| JP | 2006149863 A | 6/2006 |
| JP | 3226132 U | 4/2020 |
| TW | M347809 U | 12/2008 |
| TW | I649530 B | 2/2019 |
| WO | 2015098427 A1 | 7/2015 |
| WO | 2021003950 A1 | 1/2021 |
| WO | 2021027014 A1 | 2/2021 |
| WO | 2021027261 A1 | 2/2021 |
| WO | 2021253682 A1 | 12/2021 |

OTHER PUBLICATIONS

The International Search Report issued in corresponding International Application No. PCT/CN2020/124733, mailed Jul. 15, 2021, pp. 1-4, Beijing, China.
The Extended European Search Report issued in corresponding EP Application No. EP21162458.0, mailed Mar. 9, 2021.
The GB Search Report issued in corresponding GB Application No. GB2103494.7, mailed Aug. 10, 2021.
The physical product with model number UI04 and product name "Ulike Sapphire Hair Removal Device" (Notarization Certificate (2020) Shen Xian Zheng Zi No. 20694), (On Jun. 10, 2020, Shenzhen Yangwo Electronics Co., Ltd. applied for preservation certificate notarization to the Shenzhen Advanced Notary Office in Guangdong Province, People's Republic of China) (24 pages).
2000 Reliability Principles of Electronic Product Design Encyclopedia; published on May 2013, published in China Machine Press, ISBN 978-7-111-41985-3 (19 pages).
LED Thermal Management and Heat Dissipation Technology Application; published on Sep. 2018, published in Shanghai Scientific and Technical Publishers, ISBN 978-7-5478-4109-9 (35 pages).
Patent Infringement Determination Consultatio Report for Chinese application No. 201720489264.7. The petitioner is Shenzhen Yangwo Electronics Co., Ltd.; Request date on Sep. 24, 2020; published in Zhejiang Provincial Intellectual Property Research and Service Center (52 pages).
CNIPA, Chinese Utiliyu Patent Application No. 2020022365212.3, filing date: Oct. 23, 2020 (29 pages).

* cited by examiner

DEPILATOR

CROSS-REFERENCE TO RELATED APPLICATION(S)

This application is a continuation of Chinese Patent application No. CN2020105708074, filed Jun. 19, 2020, and Chinese Patent application No. CN2020111349308, filed Oct. 21, 2020, and PCT application No. PCT/CN2020/118788, filed Sep. 29, 2020, and PCT application No. PCT/CN2020/124733, filed Oct. 29, 2020, the disclosure of which is hereby incorporated by reference in their entirety.

TECHNICAL FIELD

The present disclosure relates to a field of electronic devices, and in particular to a depilator.

BACKGROUND

Currently, a heat conducting structure in a depilator is not efficient, resulting in that the heat of a cold compressing portion of the depilator cannot be effectively reduced, and the user is likely to cause skin burns during use, that is, the current depilator is not safe.

SUMMARY

The present disclosure provides a depilator with high heat conducting efficiency, fast cooling, and excellent safety performance.

The present disclosure provides a depilator. The depilator includes a cold compressing portion, a heat sink assembly and a heat conducting plate which are located away from the cold compressing portion. The heat conducting plate includes a main heat absorbing portion and a heat outputting portion away from the main heat absorbing portion. The main heat absorbing portion is in contact with the cold compressing portion, to absorb heat of the cold compressing portion. The heat outputting portion is in contact with the heat sink assembly, to conduct the heat to the heat sink assembly. The depilator defines a cooling channel. The depilator includes a housing. The housing defines at least one cooling inlet and at least one cooling outlet. The cooling channel is formed between the at least one cooling inlet and the at least one cooling outlet. The heat of the heat sink assembly is dissipated through the cooling channel and the at least one cooling outlet.

The depilator provided by this present disclosure absorbs the heat of the cold compressing portion through the heat conducting plate and dissipates the heat through the heat sink assembly, so that the heat of the cold compressing portion is rapidly reduced.

BRIEF DESCRIPTION OF THE ACCOMPANYING DRAWINGS

In order to explain the technical solutions of the embodiments of the present disclosure more clearly, the following will briefly introduce the drawings that need to be used in the embodiments. Obviously, the drawings in the following description are some embodiments of the present disclosure, for those of ordinary skill in the art, other drawings can be obtained based on these drawings without creative work.

DETAILED DESCRIPTION OF ILLUSTRATED EMBODIMENTS

Figure 1:
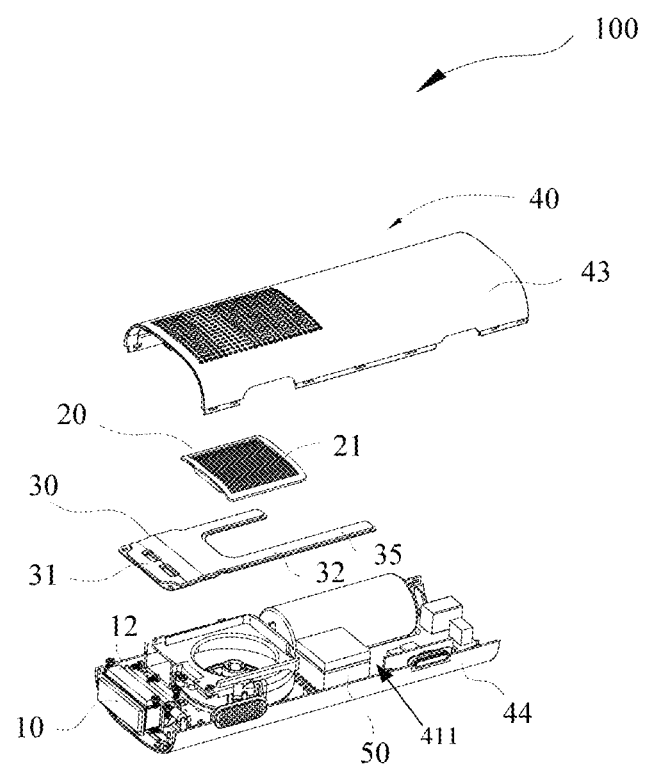
FIG. 1 is an exploded schematic view of a depilator provided by a first embodiment of the present disclosure.

The technical solutions in the embodiments of the present disclosure will be described clearly and completely with reference to the accompanying drawings in the embodiments of the present disclosure. Obviously, the described embodiments are only a part of the embodiments of the present disclosure, not all the embodiments. Based on the embodiments in this present disclosure, all other embodiments obtained by a person of ordinary skill in the art without creative work shall fall within a protection scope of the present disclosure.

In the description of the embodiments of the present disclosure, it should be understood that the orientation or positional relationship indicated by a term "thickness" is based on an orientation or a positional relationship shown in the drawings, which is only for the convenience of describing the present disclosure and simplifying the description, and does not imply the device or the element must have a specific orientation, be constructed and operated in a specific orientation, and therefore cannot be understood as a limitation of the present disclosure.

Figure 2:
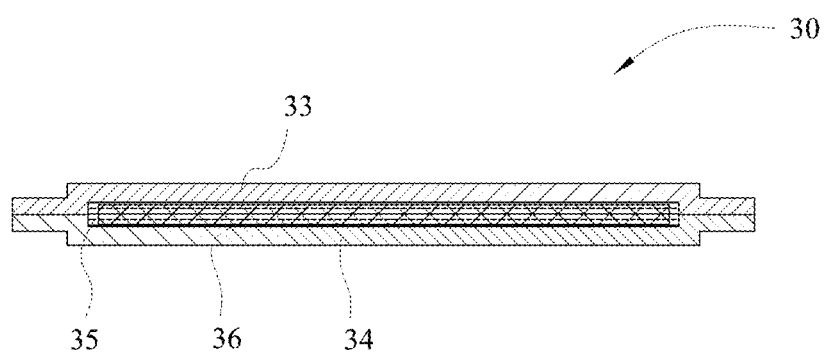
FIG. 2 is a cross-sectional view of a heat conducting plate of the depilator provided by the first embodiment of the present disclosure.

Referring to FIGS. 1 and 2, a first embodiment of the present disclosure provides a depilator 100. The depilator 100 includes a cold compressing portion 10, a heat sink assembly 20 and a heat conducting assembly which are located away from the cold compressing portion 10. The heat conducting plate 30 includes a main heat absorbing portion 31 and a heat outputting portion 32 located away from the main heat absorbing portion 31. The main heat absorbing portion 31 is in contact with the cold compressing portion 10, to absorb heat of the cold compressing portion 10. The heat outputting portion 32 is in contact with the heat sink assembly 20, to conduct heat to the heat sink assembly 20.

Therefore, the heat of the cold compressing portion 10 is absorbed by the heat conducting plate 30 and the heat is dissipated through the heat sink assembly 20, so that the heat of the cold compressing portion 10 can be quickly reduced. The depilator 100 uses the cold compressing portion 10 to contact a skin of a user, the light emitted from the cold compressing portion 10 penetrates the skin to irradiate hair follicles for depilation. The cold compressing portion 10 can quickly cool down to reduce a burning sensation caused by light and ensure comfort.

In this embodiment, the heat conducting plate 30 is VC (vapor chamber) uniform temperature plate. The heat conducting plate 30 includes a first plate 33, a second plate 34 superimposed on the first plate 33, a heat conducting medium 35 and a heat conducting net 36 which are sealed between the first plate 33 and the second plate 34. The first plate 33, the second plate 34, the heat conducting medium 35 and the heat conducting net 36 are used to absorb the heat from the heat absorbing portion 31 and conduct the heat to the heat outputting portion 32. The heat conducting net 36 is attached to the first plate 33 and the second plate 34 so that the heat conducting plate 30 conducts the heat evenly.

Because the heat conducting plate 30 includes the first plate 33, the second plate 34 superimposed on the first plate 33, and the heat conducting medium 35 and the heat conducting net 36 sealed between the first plate 33 and the second plate 34, so the heat conducting efficiency of the heat conducting plate 30 is increased; the main heat absorbing portion 31 of the heat conducting plate 30 absorbs the heat of the cold compressing portion 10, and the heat outputting portion 32 of the heat conducting plate 30 dissipates the heat through the heat sink assembly 20, the heat of the cold compressing portion 10 is thus reduced quickly.

Figure 3:
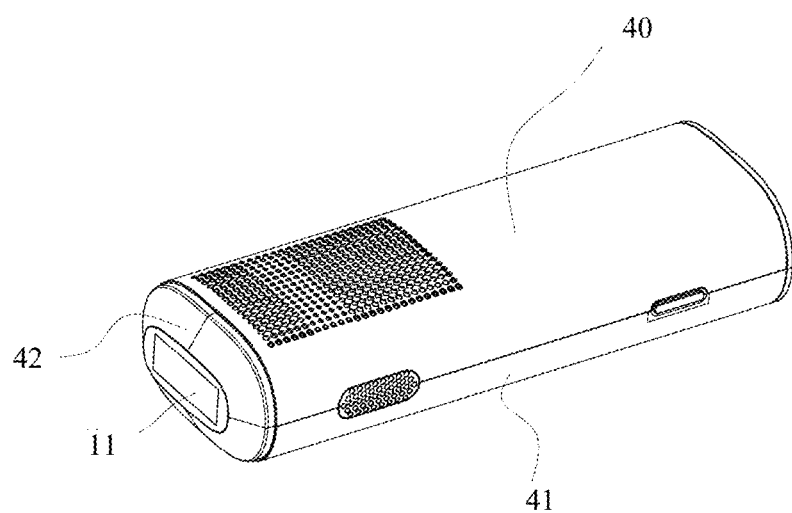
FIG. 3 is a three-dimensional schematic view of the depilator provided by the first embodiment of the present disclosure.

Referring to FIGS. 1, 2 and 3, in this embodiment, the depilator 100 includes a housing 40. The housing 40 has a hand-held portion 41 and a head portion 42 opposite to the hand-held portion 41. The cold compressing portion 10 is located on the head portion 42. The cold compressing portion 10 is configured to contact the skin of the user and emit light. The cold compressing portion 10 has a cold compressing surface 11. The cold compressing surface 11 is parallel to an outer surface of the head portion 42. The cold compressing portion 10 also has a heat conducting surface 12 located in the housing 40. The heat conducting surface 12 is in contact with the main heat absorbing portion 31. The heat of the cold compressing portion 10 is conducted from the heat conducting surface 12 to the main heat absorbing portion 31, so that the cold compressing portion 10 achieves a cooling effect. The hand-held portion 41 is used for the user to hold. The hand-held portion 41 includes operating components, such as buttons, a display screen, indicators light, and so on, so that the user can manipulate while holding the hand-held portion 41. The heat sink assembly 20 and the heat outputting portion 32 are located in the housing 40 and away from the head portion 42, to prevent the heat conducted by the heat outputting portion 32 and the heat sink assembly 20 from flowing back to the head portion 42. The housing 40 also has a tail end opposite to the head portion 42. The hand-held portion 41 is located between the head portion 42 and the tail end, so as to facilitate holding the depilator 100.

Optionally, the cold compressing surface 11 is a flat surface, and the heat conducting surface 12 is a flat surface.

Optionally, the cold compressing surface 11 is an end surface of the cold compressing portion 10. The heat conducting surface 12 is a side surface of the cold compressing portion 10.

The first plate 33 and the second plate 34 are both flat plates. The heat conducting net 36 is laminated between the first plate 33 and the second plate 34. The heat conducting net 36 is in full contact with the heat conducting medium 35, so that a contact area of the heat conducting medium 35 contacting the first plate 33, the second plate 34 and the heat conducting net 36 increases, and the heat conducting medium 35 can quickly absorb the heat that is absorbed by the main heat absorbing portion 31 from the cold compressing portion 10 and quickly conducts the heat to the heat outputting portion 32.

Optionally, both the first plate 33 and the second plate 34 are copper plates. The heat conducting net 36 is a copper net with a capillary structure, so that the contact area that the heat conducting medium 35 contacting the first plate 33 and the second plate 34 is increased and more even, and the heat conducting efficiency of the heat conducting plate 30 is improved.

Optionally, a vacuum sealed cavity is formed between the first plate 33 and the second plate 34, and the heat conducting medium 35 and the heat conducting net 36 are received in the sealed cavity.

Optionally, the heat conducting medium 35 is a cooling liquid, preferably water.

Optionally, an edge of the first plate 33 and an edge of the second plate 34 are sealed and pressed together, so that the heat conducting plate 30 has a stable structure and prevents heat from entering the heat conducting plate 30.

Optionally, the cold compressing portion 10 and the heat sink assembly 20 respectively contact two opposite surfaces of the heat conducting plate 30. For example, the first plate 33 is in contact with the cold compressing portion 10 at the main heat absorbing portion 31; the second plate 34 is in contact with the heat sink assembly 20 at the heat outputting portion 32, so that the heat sink assembly 20 absorbs the heat and then dissipates it, and the heat of the cold compressing surface 11 can be effectively reduced.

The heat sink assembly 20 includes a plurality of heat sinks 21 arranged equidistantly. One end of each heat sink 21 contacts the heat outputting portion 32, so that the heat of the heat outputting portion 32 can be quickly conducted to the heat sink 21. The gap between the heat sinks 21 is used for external cooling medium to pass through, so that the heat absorbed by the heat sinks 21 can be absorbed and taken away by the external cooling medium, to realize effective heat dissipation of the heat outputting portion 32.

Figure 4:
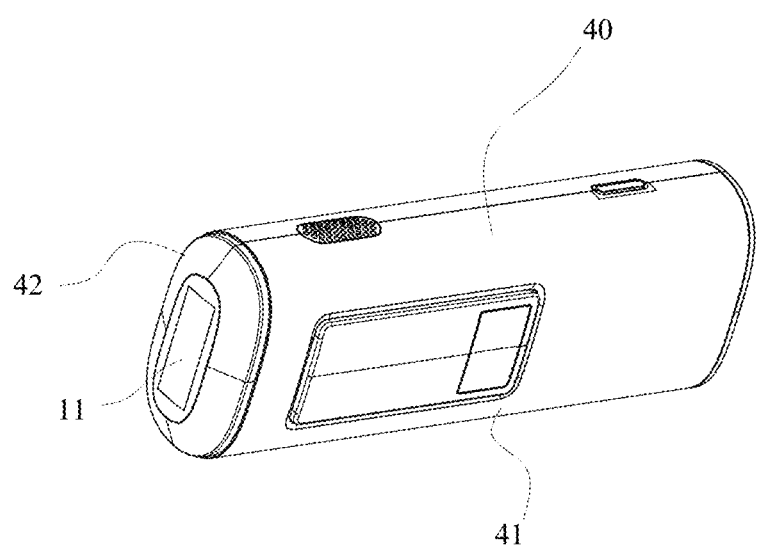
FIG. 4 is another three-dimensional schematic view of the depilator provided by the first embodiment of the present disclosure.
Figure 5:
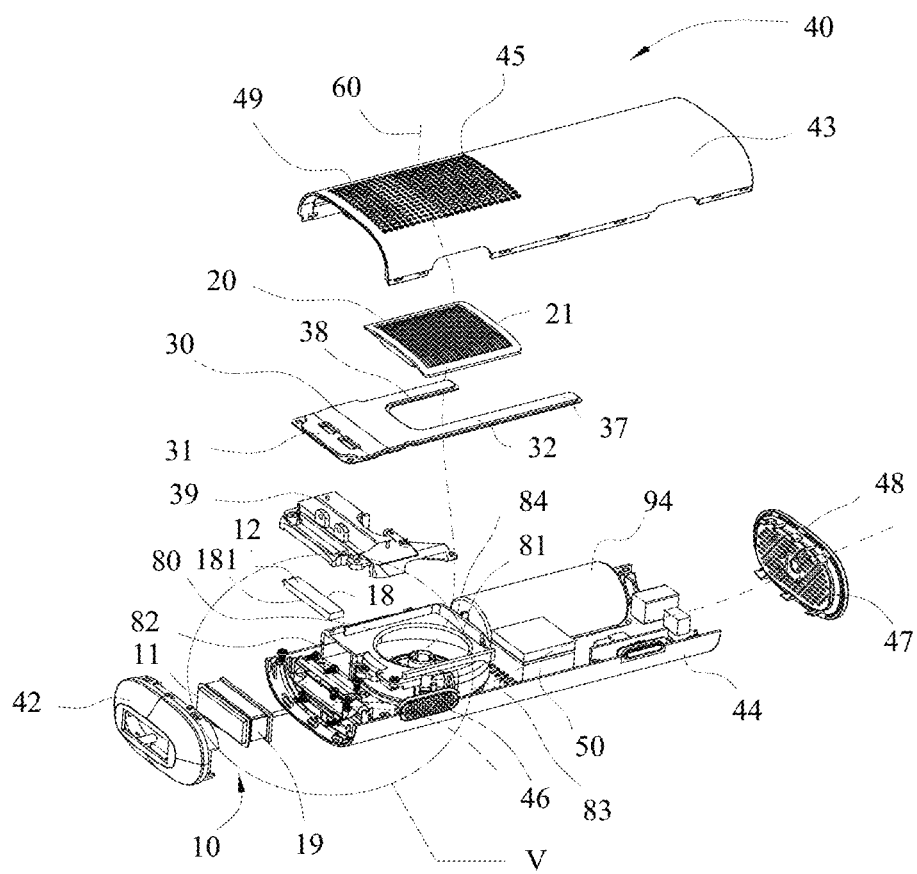
FIG. 5 is another exploded schematic view of the depilator provided by the first embodiment of the present disclosure.

Referring to FIGS. 4 and 5, as an embodiment, the housing 40 includes an upper housing 43 and a lower housing 44. The upper housing 43 and the lower housing 44 can be assembled by screwing or clamping, or can be integrated by processing. Optionally, the upper housing 43 and the lower housing 44 are assembled by snap-fitting, so as to facilitate the disassembly and the maintenance of the upper housing 43 and the lower housing 44.

Figure 8:
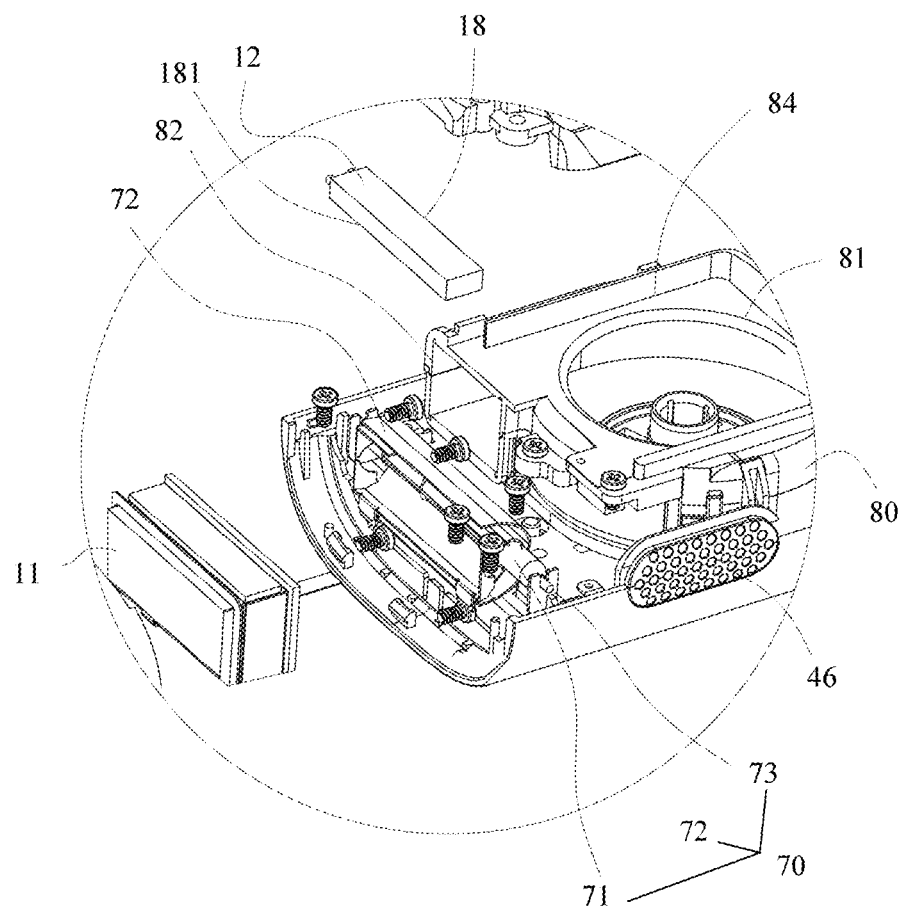
FIG. 8 is an enlarged schematic view of part V of the depilator of FIG. 5.

In this embodiment, the housing 40 defines a receiving space 411. The heat conducting plate 30 and the heat sink assembly 20 are both fixed in the receiving space 411. The depilator 100 further includes a heat removal assembly 70 (as shown in FIG. 8), a circuit device, and a power supply device received in the receiving space 411. The heat removal assembly 70, the circuit device, and the power supply device are all electrically connected in sequence. The power supply device can provide power to the heat removal assembly 70 so that the depilator 100 can be used without plugging in an external circuit. The depilator 100 can also directly use an external power supply, such as dry Capacitors, or energy storage capacitors, which is convenient to store and carry, and can be used outside. The circuit device can be connected to an external circuit to charge the power supply device, and can control a start, a stop, power regulation, and heat protection, and the like of the depilator 100.

It can be understood that the heat inside a fuselage of a traditional depilator is large at present, which is likely to cause short-circuit, burnout, explosion and other hazards to the components inside the fuselage of the depilator. The heat conducting plate 30 of the present disclosure can not only effectively cool down the cold compressing portion 10, so that the cold compressing portion 10 can effectively cold compress the skin of the user with high comfort and no damage to the skin, but also cool down the components in the receiving space 411 of the depilator 100, so that the fuselage of the depilator 100 is fully cooled, which can prevent internal temperature of the depilator 100 from over heating and causing harm. Specifically, the components in the heat removal assembly 70, the circuit device, and the power supply device of the depilator 100 of the present disclosure all generate heat during operation, the heat conducting plate 30 can be in contact with at least part of the heating deices 50 of the heat removal assembly 70, the circuit device, and the power supply device, to absorb the heat of the heating deices 50 in the heat removal assembly 70, the circuit device, and the power supply device, so that the heat in the heat removal assembly 70, circuit device, and power supply device can be removed by the heat conducting plate 30, to achieve rapid cooling of the internal components of the depilator 100, avoid excessive heat in the receiving space 411 of the depilator 100, and prevent the heat removal assembly 70, the circuit devices, and the power supply devices and other devices from dangerous situation such as short-circuiting, burning, and explosion.

Circuit devices often have some of their control components set on a surface of the housing. For example, components such as control buttons, power switches, and the like are set on the surface of the hand-held portion 41. The user can control the depilator 100 by manipulating a power switch to adjust a start, a stop, and a gear control of the depilator 100.

The heat removal assembly 70 is arranged in the receiving space 411 and close to the head portion 42, and can be fixed in the receiving space 411 of the housing 40. The circuit device and the power supply device are both installed inside the housing 40, optionally inside the hand-held portion 41. In this embodiment, they are installed on a back side of the heat removal assembly 70, which is one side of the heat removal assembly 70 away from the human skin. The design expands a contact range of the external cooling medium allowed in the receiving space 411 to achieve an overall cooling effect inside the housing 40.

Furthermore, referring to FIG. 5, the depilator 100 further includes a plurality of heating deices 50. The heat conducting plate 30 further has a plurality of secondary heat absorbing portions 37. The secondary heat absorbing portions 37 are respectively in contact with at least part of the heating deices 50, to absorb the heat of the heating deices 50.

In this embodiment, the plurality of heating deices 50 are elements provided in the heat removal assembly 70, the circuit device, and the power supply device. The plurality of heating deices 50 may be arranged in a plurality of positions in the receiving space 411. The secondary heat absorbing portion 37 extends from one side of the heat outputting portion 32. The secondary heat absorbing portion 37 and the main heat absorbing portion 31 are respectively located on both sides of the heat outputting portion 32, that is, the heating deices 50 are located away from the cold compressing portion 10, so as to prevent the heat of the heating deices 50 from being conducted to the cold compressing portion 10, and ensure the cooling effect of the cold compressing portion 10. The heating deices 50 and the cold compressing portion 10 are in contact with a same surface of the heat conducting plate 30. For example, both the heating deices 50 and the cold compressing portion 10 are in contact with one surface of the first plate 33, and the heat sink assembly 20 is in contact with one surface of the second plate 34. It can be understood that the first plate 33 can effectively absorb the heat of the cold compressing portion 10 and the heating deices 50 from the main heat absorbing portion 31 and the secondary heat absorbing portion 37, and conduct the heat to the second plate 36 through the heat conducting medium 35 and the heat conducting net 36, and the second plate 34 conducts the heat to the heat sink assembly 20 or directly dissipates from the heat outputting portion 32, so as to effectively reduce the heat of the cold compressing portion 10 and the heating deices 50.

In this embodiment, the heat conducting plate 30 covers the cold compressing portion 10, the heating deices 50 and the heat sink assembly 20, so that the heat conducting medium 35 can quickly absorb the heat of the cold compressing portion 10 and the heating deices 50, and quickly conduct the heat to the heat sink assembly 20. The heat conducting net 36 has a larger arrangement area on the first plate 33 and the second plate 34, which effectively increases the heat conducting efficiency of the heat conducting plate 30.

Figure 6:
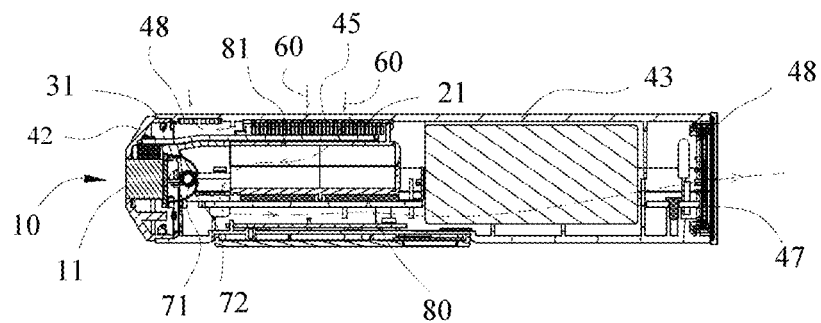
FIG. 6 is a cross-sectional view of the depilator provided by the first embodiment of the present disclosure.
Figure 7:
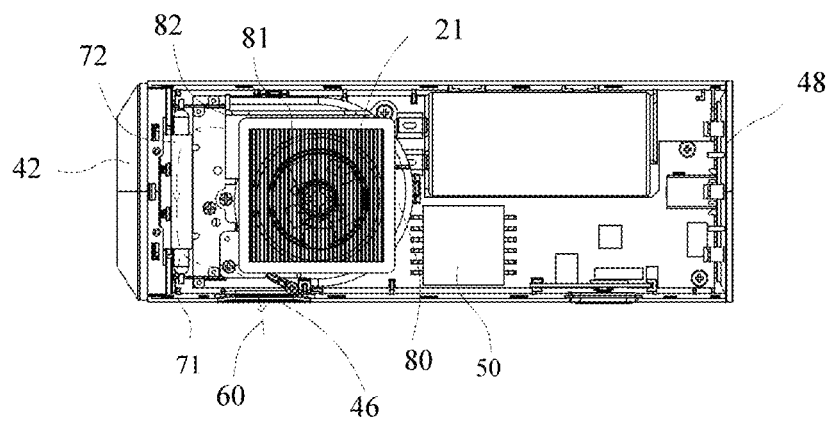
FIG. 7 is another cross-sectional view of the depilator provided by the first embodiment of the present disclosure.

Furthermore, referring to FIGS. 5, 6 and 7, the depilator 100 defines a cooling channel 60 (shown by a dashed line in FIG. 5). The cooling channel 60 introduces external cooling medium. The heat outputting portion 32, the secondary heat absorbing portion 37, the heating deices 50 and the heat sink assembly 20 are all located in the cooling channel 60.

In this embodiment, the housing 40 defines a cooling inlet 45, a first cooling outlet 46, a second cooling outlet 47, and a third cooling outlet 49. The cooling channel 60 is formed between the cooling inlet 45 and the first cooling outlet 46, and is formed between the cooling inlet 45 and the second cooling outlet 47, and is also formed between the cooling inlet 45 and the third cooling outlet 49. The cooling inlet 45 and the first cooling outlet 46 are defined on the hand-held portion 41. The first cooling outlet 46 is defined on a peripheral side of the housing 40, so that the first cooling outlet 46 can be close to an inner middle position of the depilator 100, which is convenient for discharging the heat in the inner middle position of the depilator 100. The housing 40 defines the first cooling outlet 46, the second cooling outlet 47 and the third cooling outlet 49, such that the cooling channel 60 has three parts. The first part of the cooling channel 60 is formed between the cooling inlet 45 and the first cooling outlet 46, to directly discharge the most heat of the cold compressing portion 10. The second part of the cooling channel 60 is formed between the cooling inlet 45 and the third cooling outlet 49, to contact the heat conducting plate 30 through the cold compressing portion 10, so that the heat of the cold compressing portion 10 is conducted to the heat conducting plate 30, and then dissipated through the third cooling outlet 49. The third part of the cooling channel 60 is formed between the cooling inlet 45 and the second cooling outlet 47, to dissipate the heat of the heating deice 50 through the second cooling outlet 47. The cooling inlet 45, the first cooling outlet 46 and the third cooling outlet 49 are all defined on the hand-held portion 41. The first cooling outlet 46 is defined on the peripheral side of the hand-held portion 41. The cooling inlet 45 and the third cooling outlet 49 are defined on a same side of the hand-held portion 41. The third cooling outlet 49 is adjacent to the cooling inlet 45. This design is to enable the heat of the cold compressing portion 10 to be distinguished at the same time, and the cooling medium can be sucked and discharged quickly, which improves the cooling efficiency of the cold compressing portion 10. The second cooling outlet 47 is defined at the tail end 48 of the housing 40, that is, at the end of the housing 40 away from the head portion 42. The reason why the second cooling outlet 47 is arranged farther from the cooling inlet 45 is to increase a distance through which the cooling medium flows, make the cooling range wider.

In this embodiment, the depilator 100 defines the cooling channel 60. The external cooling medium is introduced into the cooling channel 60. The heat outputting portion 32, the secondary heat absorbing portion 37, the heating deices 50 and the heat sink assembly 20 are all located in the cooling channel 60. Their heat can be effectively absorbed by the cooling medium to achieve cooling, and the overall temperature in the receiving space 411 inside the depilator 100 can be reduced. The cold compressing portion 10 is completely isolated from the cooling channel 60, so that the cooling of the cold compressing portion 10 is independent of the cooling of the heat conducting plate 30, the heat sink assembly 20, and the heating deices 50.

In this embodiment, the heat outputting portion 32 of the heat conducting plate 30 and the heat sink assembly 20 are adjacent to the cooling inlet 45. The heating deices 50 are adjacent to the first cooling outlet 46 and the second cooling outlet 47. The cooling channel 60 introduces the external cooling medium from the cooling inlet 45 so that the external cooling medium preferentially contacts the heat outputting portion 32 of the heat conducting plate 30 and the heat sink assembly 20 so that the heat of the heat outputting portion 32 of the heat conducting plate 30 and the heat sink assembly 20 is preferentially absorbed by the cooling medium to achieve rapid cooling. After the cooling medium passes through the heat sink assembly 20 and the heat outputting portion 32 of the heat conducting plate 30, it continues to flow to the plurality of the heating deices 50, so that the heat of the heating deices 50 is absorbed by the cooling medium and taken away by the cooling medium, and the cooling medium finally flows out from the first cooling outlet 46 and the second cooling outlet 47 to achieve overall effective heat dissipation.

Optionally, the heat sink assembly 20 and the cooling inlet 45 are sealed and abutted, so that the heat sink assembly 20 effectively receives the external cooling medium that enters from the cooling inlet 45, and reduces a flow resistance of the heat sink assembly 20 to the external cooling medium, to ensure the heat conducting efficiency. The heat outputting portion 32 of the heat conducting plate 30 is in contact with one side of the heat sink assembly 20 away from the cooling inlet 45.

Optionally, the heat conducting plate 30 defines a through slot 38, and the through slot 38 forms a part of the cooling channel 60. The heat outputting portion 32 is arranged on a peripheral side of the through slot 38. After the external cooling medium passes through the heat sink assembly 20, it flows through the through slot 38, so that the heat outputting portion 32 is in contact with the external cooling medium. Of course, part of the cooling medium flows through the main heat absorbing portion 31 and the secondary heat absorbing portion 37 of the heat conducting plate 30 after passing through the heat sink assembly 20, so that the main heat absorbing portion 31 and the secondary heat absorbing portion 37 are effectively cooled.

Referring to FIGS. 5 and 8, in this embodiment, the heat removal assembly 70 includes a lamp tube 71, a reflecting plate 72 and a lamp tube holder 73. The lamp tube 71, the reflecting plate 72 and the lamp tube holder 73 are all located in the cooling channel 60. The lamp tube 71, the reflecting plate 72 and the lamp tube holder 73 are all fixed in a part of the receiving space 411 adjacent to the head portion 42, to reduce a path of the light emitted by the lamp tube 71 and prevent the heat of the emitted light from being conducted to more devices, so as to decrease heat gathered in the receiving space 411. The lamp tube 71, the reflecting plate 72 and the lamp tube holder 73 are adjacent to the first cooling outlet 46, so that the cooling medium can immediately discharge the heat from the first cooling outlet 46 after absorbing the heat of the lamp tube 71, the reflecting plate 72 and the lamp tube holder 73, effectively reduce the heat of the lamp tube 71, the reflecting plate 72 and the lamp tube holder 73. The lamp tube 71 is directly opposite to the cold compressing portion 10, and the light emitted by the lamp tube 71 exits through the cold compressing portion 10. The reflecting plate 72 is located on one side of the lamp tube 71 away from the cold compressing portion 10. The reflecting plate 72 condenses and reflects the light of the lamp tube 71, to increase the light concentration of the cold compressing portion 10. The two ends of the reflecting plate 72 have openings, so that the cooling medium flows through one opening of the reflecting plate 72 to the other opening, and the external cooling medium contacts the peripheral side of the lamp tube 71 to form convection and effectively cool the lamp tube 71. The lamp tube holder 73 fixes both ends of the lamp tube 71. It can be understood that both the reflecting plate 72 and the lamp tube holder 73 can form the heating deices 50. That is, the secondary heat absorbing portion 37 of the heat conducting plate 30 can be in contact with the reflecting plate 72 and the lamp tube holder 73, so that the heat conducting plate 30 can effectively absorb the heat of the reflecting plate 72 and the lamp tube holder 73, and reduce the heat of the reflecting plate 72 and the lamp tube holder 73, thereby reducing the heat of the heat removal assembly 70 as a whole, and further reducing the heat of the cold compressing portion 10.

Figure 9:
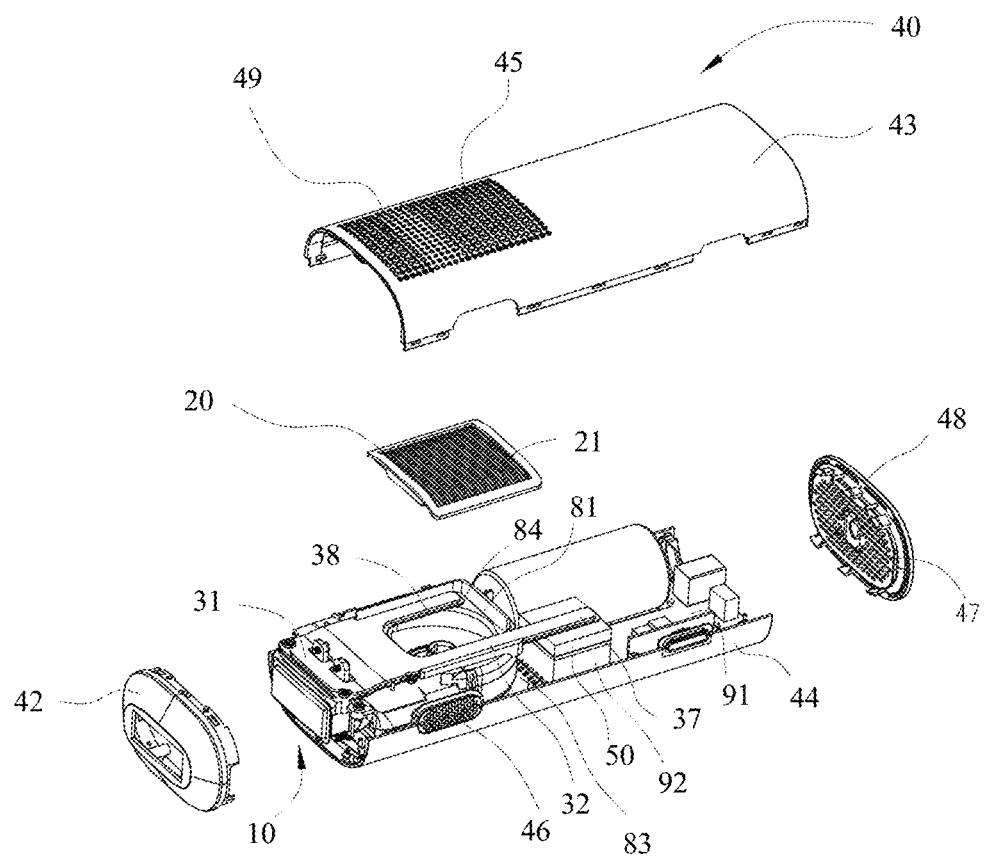
FIG. 9 is another schematic view of the depilator provided by the first embodiment of the present disclosure.

Furthermore, please continue to refer to FIG. 5, FIG. 8 and FIG. 9, the depilator 100 includes a cool driving portion 80 arranged in the cooling channel 60. The cool driving portion 80 is configured to drive the external cooling medium in the cooling channel 60 to flow.

In this embodiment, the cool driving portion 80 is fixed in the receiving space 411 and located at a portion of the heat removal assembly 70 away from the cold compressing portion 10. The cool driving portion 80 drives the external cooling medium in the cooling channel 60 to flow through a power device, so that the external cooling medium can effectively take away the heat in the depilator 100. The cool driving portion 80 defines a driving inlet 81 and a driving outlet 82. The driving inlet 81 is directly opposite to the through slot 38, so that the external cooling medium can quickly flow through the heat sink assembly 20 and the heat outputting portion 32 of the heat conducting plate 30, to effectively cool down the heat outputting portion 32 of the heat conducting plate 30. The driving outlet 82 is opposite to the heat removal assembly 70 so that the external cooling medium can be guided to the lamp tube 71, the reflecting plate 72 and the lamp tube holder 73 intensively, and the flow rate of the cooling medium around the heat removal assembly 70 is increased.

Optionally, the cool driving portion 80 is a fan. The external cooling medium is air. For example, the cool driving portion 80 is a centrifugal fan, an axial fan, a mixed flow fan, and a cross flow fan. Preferably, the cool driving portion 80 is a centrifugal fan, so that the external air flows mainly in the radial direction after entering an impeller of the fan axially.

Specifically, the cool driving portion 80 includes a shell 83 and a fan blade fixed in the shell 83. The driving inlet 81 and the driving outlet 82 are defined in the shell 83. The bottom of the shell 83 is fixed on inner side of the lower housing 44. The driving inlet 81 is defined on a top of the shell 83. The driving outlet 82 is defined on a peripheral side of the shell 83. The heat conducting plate 30 is fixed on the top of the shell 83. The shell 83 effectively supports the heat conducting plate 30, so that the heat outputting portion 32 of the heat conducting plate 30 is effectively stabilized. The depilator 100 also includes a heat conducting support 39 fixed in the housing 40 and stably connected with the shell 83. The heat conducting support 39 effectively supports the main heat absorbing portion 31 of the heat conducting plate 30. The heat conducting support 39 isolates the cooling medium of the driving outlet 82 from the heat conducting plate 30, to avoid the cooling medium at the driving outlet 82 from flowing back to the heat conducting plate 30, and to ensure that the heat conducting plate 30 effectively cools the cold compressing portion 10.

More specifically, the top of the shell 83 defines a fixing groove 84. The heat conducting plate 30 passes through the fixing groove 84. The heat sink assembly 20 is fixed in the fixing groove 84. The driving inlet 81 is arranged at a bottom of the fixing groove 84. The heat sink assembly 20 is in sealing engagement with a circumferential side of the fixing groove 84, to reduce a wind resistance between the heat sink assembly 20 and the driving inlet 81.

Optionally, the heat sink 21 in the heat sink assembly 20 may be a cast iron heat sink, a steel heat sink, or an aluminum alloy heat sink. It can be understood that the heat sink 21 dissipates heat in a form of convection, so the larger the coverage area, the better the heat dissipation effect. The plurality of heat sinks 21 completely cover the driving inlet 81.

Optionally, the heat sinks 21 in the heat sink assembly 20 and the heat conducting plate 30 are an integral structure. The heat sink assembly 20 and the heat conducting plate 30 are connected together. Under the action of metal heat conduction, the external cooling medium is sucked into the depilator 100 along with the cool driving portion 80, so that the heat on the heat outputting portion 32 will be quickly discharged with the external cooling medium, thereby quickly cooling down.

More specifically, the depilator 100 further includes a circuit board 91 fixed on an inner side of the lower housing 44, a processor 92 fixed on the circuit board 91, and a capacitor 94 fixed on the inner side of the lower housing 44. The shell 83 of the cool driving portion 80 is fixed on the circuit board 91. The cool driving portion 80 is electrically connected to the circuit board 91, to obtain driving electrical signals from the circuit board 91. The processor 92 processes the electrical signal of the heat removal assembly 70 to control the operation of the heat removal assembly 70. The capacitor 94 provides power to the heat removal assembly 70, the cool driving portion 80, the circuit board 91 and the processor 92. The circuit board 91, the processor 92, the capacitor 94 and the cool driving portion 80 can all form the heating deices 50. Preferably, the secondary heat absorbing portion 37 of the heat conducting plate 30 is in contact with the processor 92. The secondary heat absorbing portion 37 absorbs heat on the processor 92, so that the heat of the processor 92 is effectively reduced. The circuit board 91, the processor 92, and the capacitor 94 are all on a path of the external cooling medium from the driving outlet 82 to the second cooling outlet 47.

Furthermore, the cold compressing portion 10 includes a cold compressing member 19 and a cooling member 18 for cooling the cold compressing member 19. The cold compressing member 19 is configured to contact the skin of the user and perform cold compresses. The cooling member 18 includes a cooling surface 181 for contacting the cold compressing member 19 and a heat conducting surface 12 opposite to the cooling surface 181. The main heat absorbing portion 31 is in contact with the heat conducting surface 12, to absorb the heat from the heat conducting surface 12.

In this embodiment, both the lamp tube 71 and the cooling member 18 are electrically connected to the circuit board 91. The cooling member 18 is fixed on the heat conducting support 39, so that the cooling member 18 is firmly fixed to between the cold compressing member 19 and the heat conducting support 39, and the main heat absorbing portion 31 is in contact with the cooling member 18. The cooling member 18 is closely in contact with the cold compressing member 19 so as to cool the cold compressing member 19. A filter is also arranged between the cold compressing member 19 and the lamp tube 71 to prevent the heat of the lamp tube 71 from being conducted to the cold compressing member 19. The reflecting plate 72 is arranged on one side of the lamp tube 71 away from the cold compressing member 19, so that the light emitted by the lamp tube 71 is concentrated on the cold compressing member 19.

Preferably, the cold compressing member 19 is made of crystal material, specifically sapphire, K9 glass, crystal glass, and all materials that meet the requirements of light-transmitting crystals may be used, and optionally, sapphire material.

Preferably, the cooling member 18 can be but is not limited to TEC (Thermoelectric Cooler) semiconductor refrigeration chip.

It can be understood that because the cold compressing member 19 is made of sapphire, the cold compressing member 19 can also be used as a light outlet. When the lamp tube 71 emits light, the sapphire has a strong heat conducting efficiency, so that the cooling member 18 and cold compressing member 19 can efficiently generate heat exchange, so as to achieve the best cooling effect. Optionally, the cold compressing member 19 can be a circular plate or a rectangular plate, which is not limited here. One surface of the cold compressing member 19 away from the lamp tube 71 is in contact with the human body, and the contact surface may be a curved surface or a flat surface, preferably a flat surface.

In this embodiment, the lamp tube 71 may be an IPL (Intense Pulsed Light) lamp tube, which is located on one side of the cold compressing member 19 away from a human body. The light emitted by the lamp tube 71 is emitted to the skin of the user through the cold compressing member 19.

The color of the light emitted by the lamp tube 71 is not limited, and can be colored light, composite light, etc. The specific wavelength and frequency are determined according to the usage.

In this embodiment, the depilator 100 includes a skin detection part, which can be integrated in the cold compressing member 19. The skin detection unit uses a capacitive touch detection principle to electrically connect the circuit board 91. When the cold compressing member 19 touches the skin, an internal preset capacitance detection device also detects whether the depilator 100 actually touches the skin, so as to reduce a safe question caused by misoperations of a user.

In this embodiment, the shape of the reflecting plate 72 is not limited, and only the light of the lamp tube 71 is concentrated in a direction of the cold compressing member 19. Optionally, the reflecting plate 72 is U-shaped, and the opening of the reflecting plate 72 faces the cold compressing member 19. The lamp tube 71 is located in a center of the U-shaped opening of the reflecting plate 72. In addition to concentrating light, it can also prevent the lamp tube 71 from dissipating heat to other places during operation.

In this embodiment, the cooling member 18 is optionally a refrigeration element in a semiconductor refrigeration mode. The cooling member 18 includes a heat conducting surface 12 and a cooling surface 181 that are arranged oppositely. The cooling surface 181 is closely attached to the cold compressing member 19 to cold compress the cold compressing member 19.

It can be understood that due to a special principle of the depilator 100 using light hair removal technology, a lot of heat will be generated when the light is emitted. At the same time, when the cold compressing member 19 touches the skin, in order to prevent the light from causing the user to have a burning sensation, the inside of the body of the depilator 100 needs to be provided with a cooling structure. No matter how the temperature is cooled, the heat will be generated under the heat exchange. The heat conducting surface 12 of the cooling member 18 is close to the main heat absorbing portion 31 of the heat conducting plate 30, making the cold compressing member 19 fast cooling. In addition to the heating of the cooling member 18, there are also the plurality of heating deices 50 in the receiving space 411. The external cooling medium in the cooling channel 60 can effectively cool the the plurality of heating deices 50.

It can be understood that the external cooling medium is sucked in from the cooling inlet 45, enters the driving inlet 81 and passes through the driving outlet 82, passes through the lamp tube 71 along the way, so that the heat of the lamp tube 71 reduces, and then passes through the circuit board 91, the processor 92 and the capacitor 94 inside the housing 40, and finally discharges from the first cooling outlet 46 and the second cooling outlet 47, thereby forming a path of the cooling channel 60 so that the cooling channel 60 cools the area passing by the external cooling medium along the way.

It can be understood that the heat conducting plate 30 and the heat sink assembly 20 are combined into one body. The outer surface of the heat conducting plate 30 and the inner wall of the housing 40 form a space. The cooling inlet 45 is attached to form another cooling channel 60, so that the heating conducting plate 30 and the cooling member 18 effectively cools down.

Based on the above setting of the cooling channel 60 in the depilator 100, in some embodiments, the heat dissipation method of the depilator 100 may not use fan air cooling, or other external cooling medium, such as water, coolant, etc., only the heat of two channels can be taken away by external cooling medium is enough.

A contact end surface of the cold compressing portion 10 with the skin and an exposed end surface of the skin detection part are located on the same side, so that when the skin is lighted and hair removed, the cold compressing member 19 contacts an irradiated area of the skin, and cold compresses the irradiated skin to cool down, so as to reduce a burning sensation of the irradiated skin, and the cold compressing member 19 can reach a low temperature close to zero, so that the skin near the light outlet can reach infinitely close to a freezing point, which can reduce the burning sensation of the skin, and short-term contact will not cause skin damage.

In some embodiments, more than the two cooling channels 60 described in this embodiment are provided. In addition to the cooling member 18 and the lamp tube 71, a plurality of cooling channels 60 can also be provided, and the plurality of cooling channels 60 can be used for cooling down the plurality of heating deices 50.

In some embodiments, the depilator 100 is provided with a luminous body, and the structural features described in all the above embodiments are used.

Figure 10:
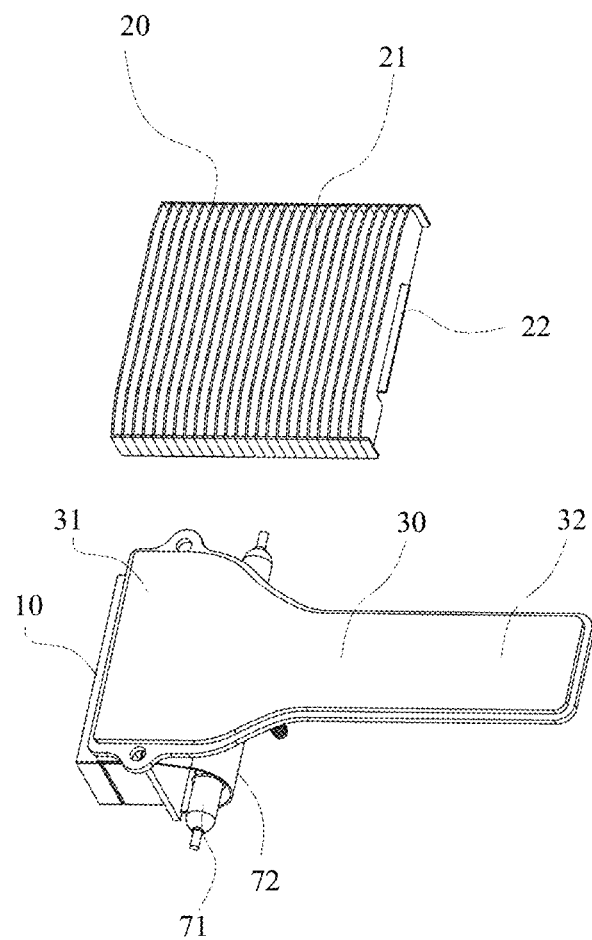
FIG. 10 is an exploded schematic view of a part of the depilator provided by a second embodiment of the present disclosure.
Figure 11:
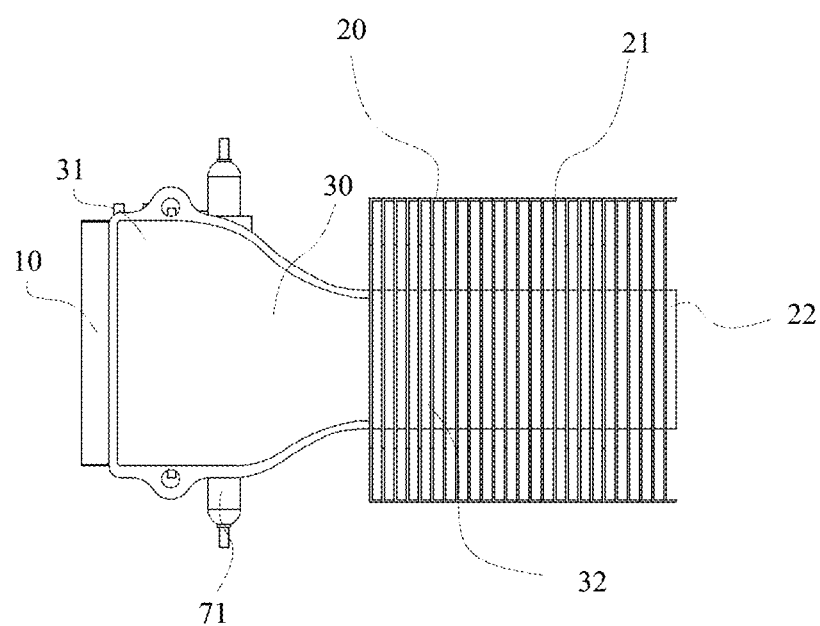
FIG. 11 is an assembly schematic view of a part of the depilator provided by the second embodiment of the present disclosure.
Figure 12:
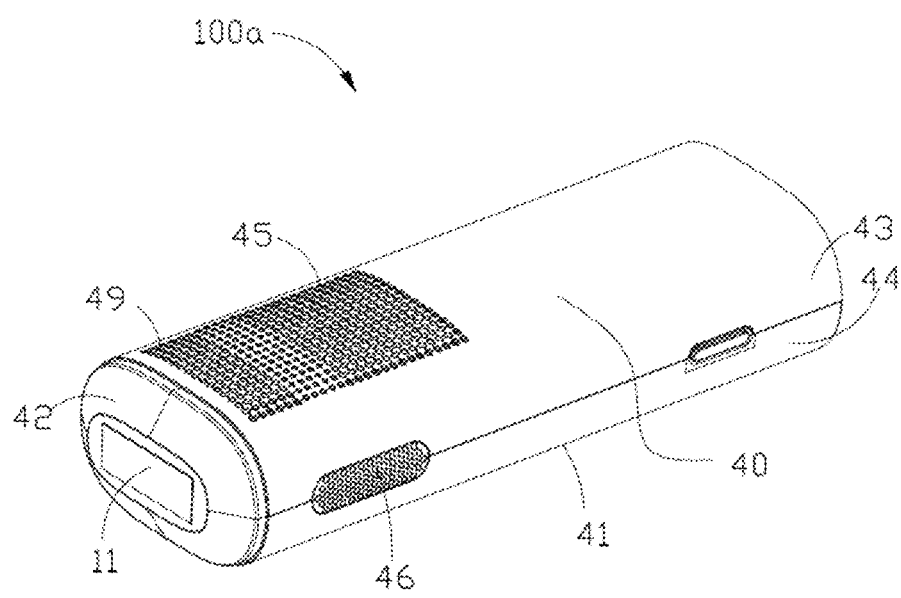
FIG. 12 is an assembly schematic view of the depilator provided by a third embodiment of the present disclosure.
Figure 13:
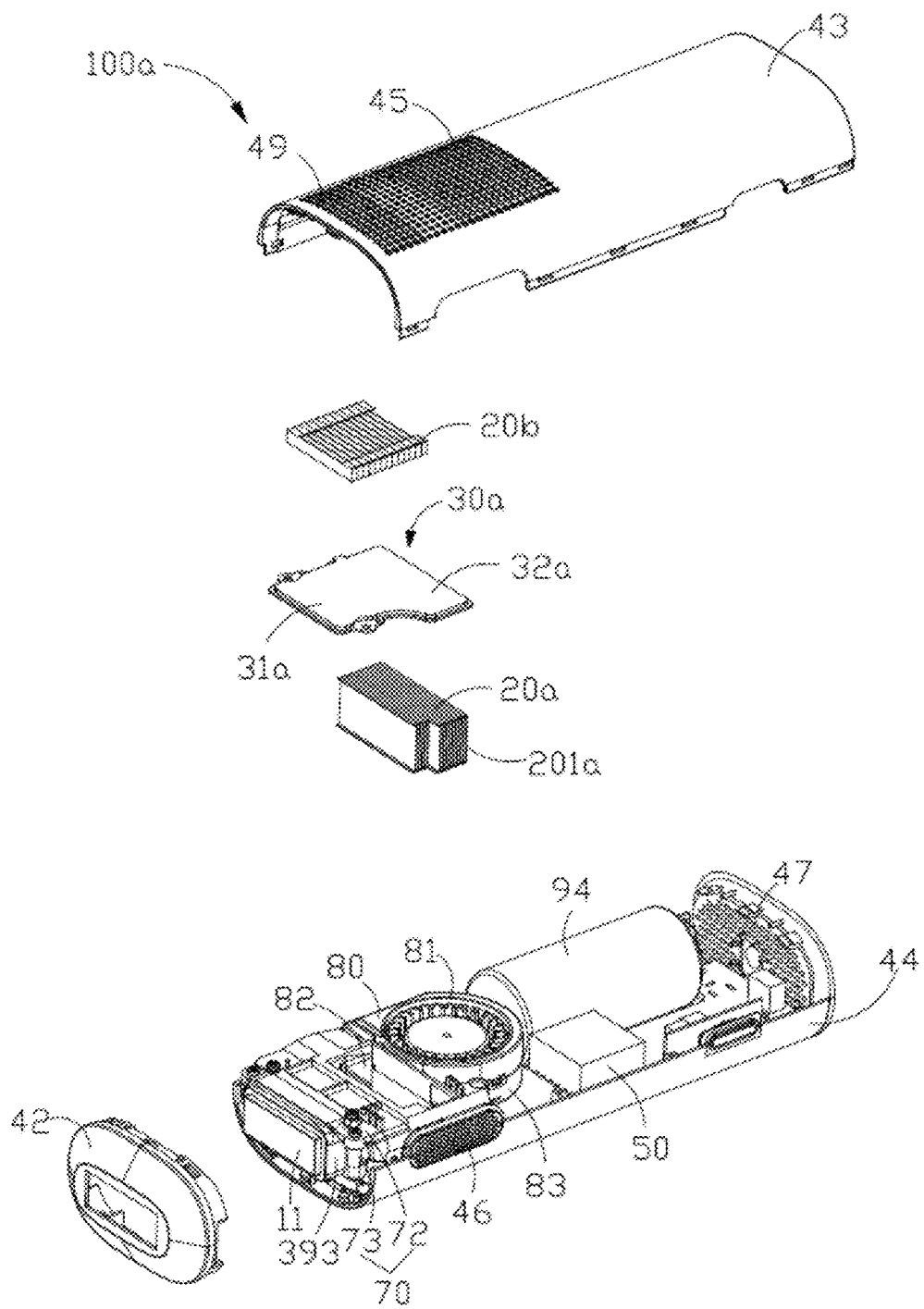
FIG. 13 is an exploded schematic view of the depilator provided by the third embodiment of the present disclosure.
Figure 14:
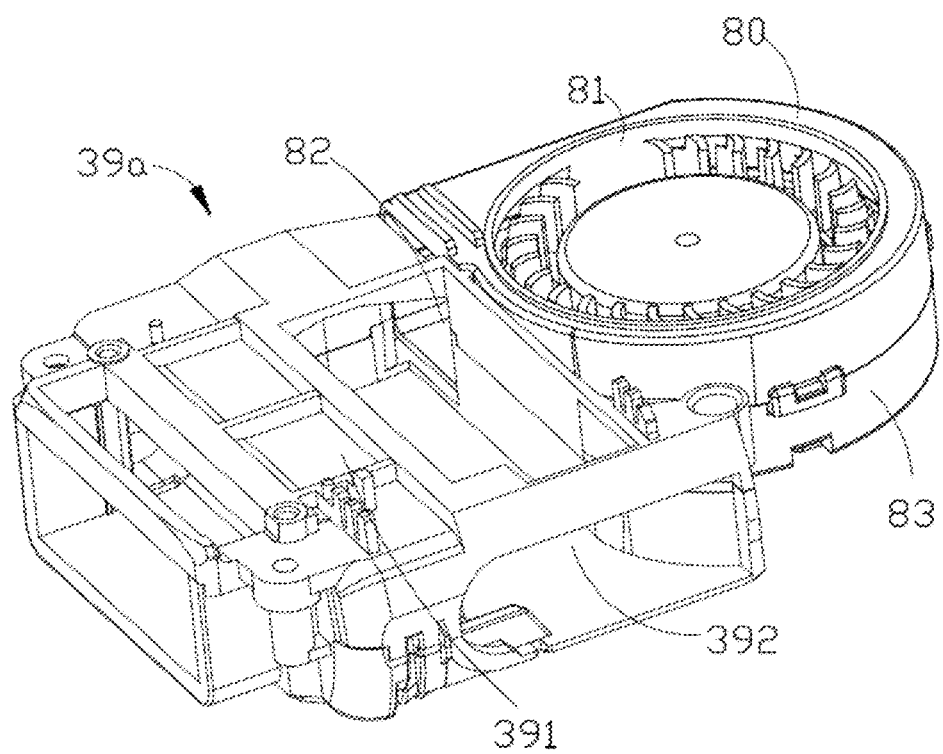
FIG. 14 is a schematic view of a part of the depilator provided by the third embodiment of the present disclosure.
Figure 15:
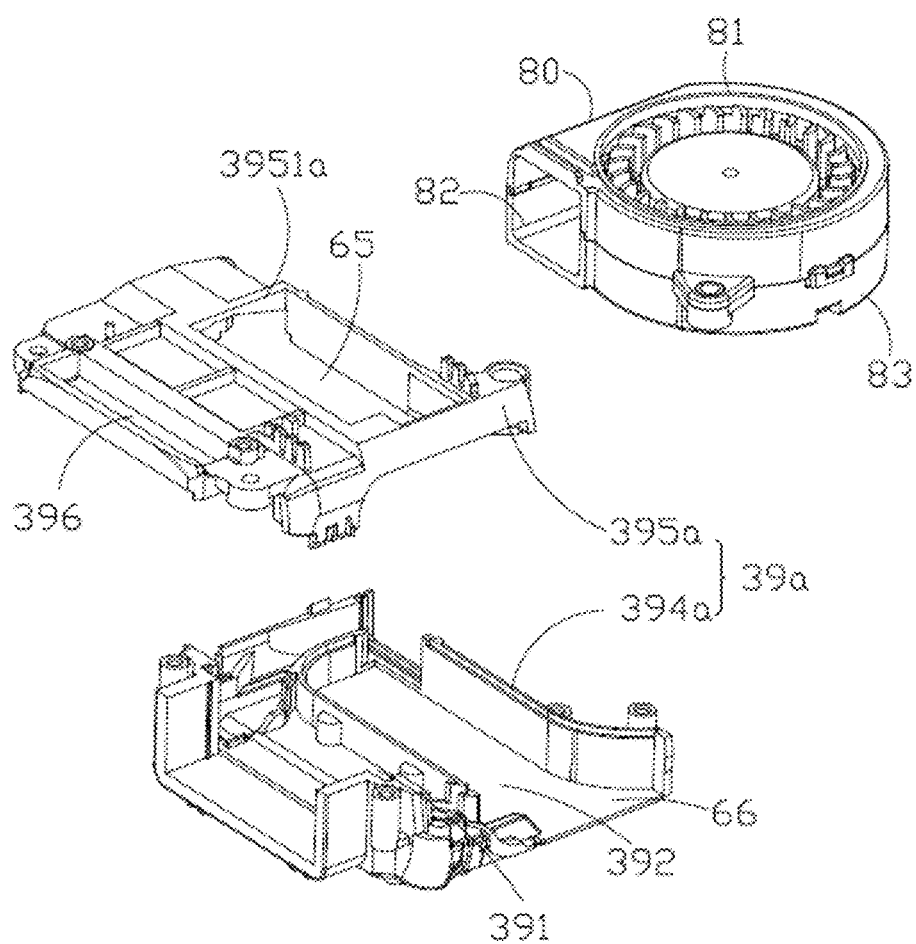
FIG. 15 is an exploded schematic view of a part of the depilator provided by the third embodiment of the present disclosure.
Figure 16:
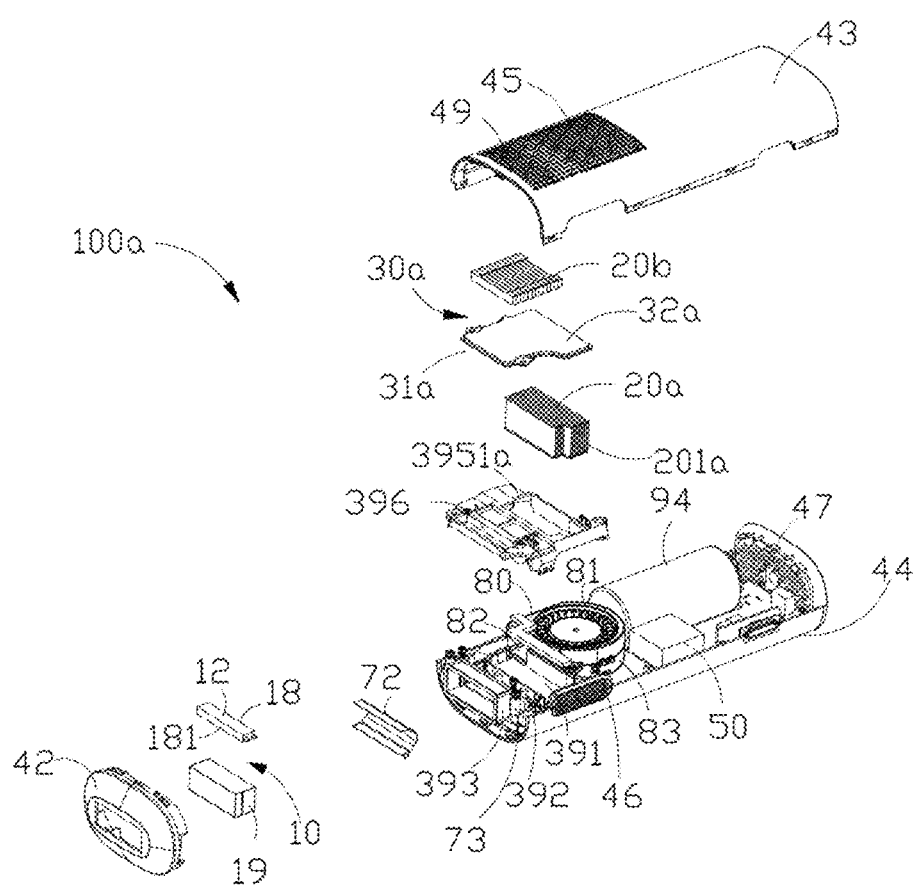
FIG. 16 is another exploded schematic view of the depilator provided by the third embodiment of the present disclosure.
Figure 17:
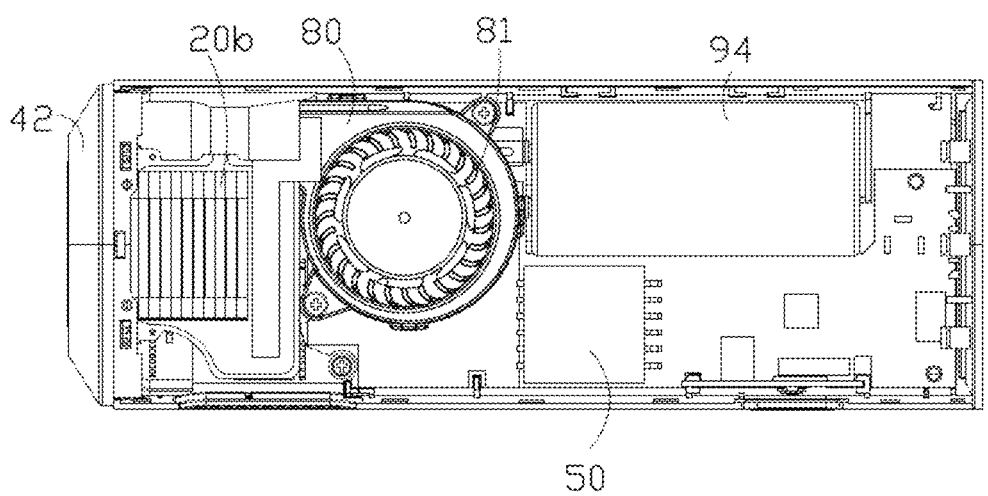
FIG. 17 is a top view of a partial structure of the depilator provided by the third embodiment of the present disclosure.

In the second embodiment, please referring to FIG. 10 and FIG. 11, which is substantially the same as the first embodiment shown in FIG. 5, except that the heat conducting plate 30 is in a "T" shape. A wider end of the heat conducting plate 30 completely covers the cold compressing portion 10 to improve a heat absorption efficiency of the cold compressing portion 10 of the heat conducting plate 30. A narrow end of the heat conducting plate 30 partially contacts the heat sink assembly 20. That is, the main heat absorbing portion 31 is arranged at the wider end of the heat conducting plate 30. The heat sink assembly 20 is provided with a bonding plate 22 (see FIG. 10) that is bonded to the plurality of heat sinks 21, and the bonding plate 22 is also bonded to the narrower end of the heat conducting plate 30, to increase the heat conducting efficiency of the narrower end of the heat conducting plate 30 and the heat sink assembly 20. That is, the heat outputting portion 32 is arranged at the narrower end of the heat conducting plate 30. The portion of the heat sinks 21 that is not covered by the heat conducting plate 30 is used to guide the cooling medium to pass, so that the heat sink assembly 20 and the heat conducting plate 30 are cooled. Of course, in other embodiments, the heat conducting plate 30 can also be arranged in any other shape.

Those skilled in the art should also understand that if all or part of the components of the depilator 100 of the present disclosure are combined by means of fusion, physical connection, etc., for example, moving positions of the components in the heat removal assembly 70; or they are integrated; or they are detachably designed; as well as the replacement of the number of features, and the change of feature shapes that are not used as functions. Any combined component can form a device/apparatus with a specific function. Using such a device/apparatus to replace the corresponding component of the present disclosure also falls the protection scope of the present disclosure.

Compared with the prior art, the depilator 100 of the present disclosure has the following advantages:

1. The depilator 100 uses the heat conducting plate 30 with a composite structure. The heat conducting plate 30 uses the first plate 33, the second plate 34 superimposed on the first plate 33, and the heat conducting medium 35 and the heat conducting net 36 sealed between the first plate 33 and the second plate 34, to increase the heat conducting efficiency of the heat conducting plate 30. The main heat absorbing portion 31 of the heat conducting plate 30 absorbs the heat of the cold compressing portion 10, and the heat outputting portion 32 of the heat conducting plate 30 dissipates the heat through the heat sink assembly 20, so that the heat of the cold compressing portion 10 is rapidly reduced. The heat conducting plate 30 is made of copper material, which increases the heat conducting efficiency of the heat conducting plate 30, so that the main heat absorbing portion 31 can effectively and quickly absorb heat, and the heat outputting portion 32 can effectively and quickly dissipate heat.

2. The depilator is a household portable depilator, which is relatively small for the convenience of use's hand holding. Therefore, in the case of a large amount of heat accumulation, if the heat can not be dissipated and cooled in time, it will bring strong pain, redness and swelling to the user, and even cause safety issues: in the past, only a single inlet and outlet were set up in the portable depilator to form a channel for heat dissipation. However, there are more than one heat-generating components inside the portable depilator. For example, a plurality of heat-generating components rely on a single inlet and outlet for heat dissipation. The heat generated by the heat-generating components will affect each other, reducing the heat dissipation effect, and the working environment of the heat-generating components in the channel will be affected; for example, the cooling member 18 and the lamp tube 71 that both generate heat are placed in the same cooling channel 60. When the cooling medium passes through one of the cooling member 18 and the lamp tube 71, it will conduct its heat to the other component. Therefore, in this present disclosure, a portable depilator 100 is provided with a plurality of cooling channels 60, and different heat generating components can be set in different cooling channels 60, its cooling channel 60 can have one inlet corresponding to a plurality of outlets, or a plurality of inlets corresponding to a plurality of outlets. Therefore, under the action of the heat conducting components, the external cooling medium can dissipate heat and reduce the temperature of multiple heat generating components inside the portable depilator 100, and will not interfere with each other.

3. Two isolated cooling channels 60 are provided to cool the cooling member 18 and the lamp tube 71 separately. Unlike the previous method that only uses a sealed cavity to protect the cooling member 18 and ventilate it separately, other heating deice 50 such as the circuit device, the power supply device, the lamp tube and the like which also generate heat are not considered, especially when used for a long time, the heat of the lamp tube 71 will be very high, so the cooling effect is not complete.

In this embodiment, this method can not only protect the airflow of the cooling member 18, but also in at least two channels, the heat on the cooling member 18 is quickly conducted by using the composite heat conducting plate 30, due to the complete isolation and the heat conduction provided by the heat conducting plate 30, the external cooling medium can only be discharged from the corresponding outlet after the heat exchange is completed. It can not only cool the cooling member 18, but also other heating deices 50 inside the depilator 100, such as the circuit board 91, the capacitor 94, the processor and the lamp tube 71, which can further improve the cooling effect of the cold compressing member 19, and reduce the cooling heat as much as possible to the cooling temperature that temporarily paralyzes the skin, thereby reducing the strong pain sensation and redness of the skin caused by hair removal.

4. The external cooling medium that can be used by the technical means of the present disclosure can be not only the introduction of air for the fan, but also other cooling mediums, such as the use of water pumps, extraction of water or cooling liquid, etc.

5. Between the driving inlet 81 of the driving cooling part and the cooling inlet 45 of the housing 40, the heat outputting portion 32 of the heat conducting plate 30 and the heat sink assembly 20 are set, and one end of the heat conducting plate 30 extends to the cooling member 18 to make the cool driving portion 80 introduce the external cooling medium, and further cool the heat conducting plate 30 and the cooling member 18 simultaneously.

6. There are three cooling outlets on the housing 40. One cooling outlet is arranged on the housing 40, and is arranged on a same side with the cooling inlet 45 and adjacent to it, so that the cooling medium can enter and discharge quickly, improve the heat conducting efficiency of the heat conducting plate 30. One cooling outlet is arranged at a lateral direction of the housing 40, that is, the side of the cold compressing portion 10, can quickly dissipate most of the heat of the cold compressing portion 10 and reduce the heat of the cold compressing portion 10. One cooling outlet is arranged at a tail end of the depilator 100 away from the cold compressing portion 10, so that the cooling medium flows in the depilator 100 and is discharged after a longer distance, so that the heat of the heating devices 50 flowing through is removed, and the heat of the heating devices 50 is reduced.

7. The cold compressing member 19 is exposed from the head portion 42 of the housing 40 and actually contacts the human skin, so that the user can feel a cold compressing effect of the cold compressing member 19 while using the depilator 100 to remove hair, thereby reducing the strong pain sensation caused by the heat generated by the depilator 100.

8. The cold compressing member 19 is made of crystal material, which can be made of sapphire. Sapphire has strong heat conductivity, which reduces the heat of the light emitted by the depilator 100 while maintaining the light transmittance.

9. The cooling member 18 can be a semiconductor refrigeration chip, which can effectively improve the cooling effect of the depilator 100.

10. The depilator 100 is equipped with a skin detection part, which is in contact with the cold compressing portion 10.

11. The heat conduction plate 30 is a VC uniform temperature plate, and its uniformity effect is better than that of heat pipes or metal substrate radiators, which can make the surface temperature more uniform (reduce hot spots). Secondly, the use of the VC uniform temperature plate allows the heat source to directly contact the VC uniform temperature plate, thereby reducing thermal resistance.

Please referring to FIGS. 12-17, FIGS. 12-17 are schematic structural diagrams of the depilator 100a in a third embodiment of the present disclosure. The third embodiment is substantially the same as the first embodiment as shown in FIG. 5, except that the heat conducting support 39 in the first embodiment can be replaced with a cooling support 39a in the third embodiment. The heat sink assembly 20 in the first embodiment can be replaced with a first heat sink assembly 20a and a second heat sink assembly 20b in the third embodiment, and the heat conducting plate 30 in the first embodiment can be replaced with a heat conducting plate 30a in the third embodiment. For the convenience of description, the combination of the first heat sink assembly 20*a*, the second heat sink assembly 20*b*, and the heat conducting plate 30*a* may be referred to as a "heat conducting assembly".

The heat conducting plate 30*a* is preferably a VC uniform temperature plate. The heat conducting plate 30*a* includes a main heat absorbing portion 31*a* and a heat outputting portion 32*a* away from the main heat absorbing portion 31*a*. The main heat absorbing portion 31*a* is in contact with the cold compressing portion 10, to absorb the heat of the cold compressing portion 10. The heat outputting portion 32*a* is in contact with the first heat sink assembly 20*a* and the second heat sink assembly 20*b*, to conduct heat to the first heat sink assembly 20*a* and the second heat sink assembly 20*b*.

The cooling bracket 39*a* defines a first cooling passage 391 and a second cooling passage 392 separated from the first cooling passage 391. The first cooling passage 391 and the second cooling passage 392 constitute a part of the cooling channel 60. The heat removal assembly 70 is fixed in the first cooling passage 391. A part of the heat conducting assembly away from the cold compressing portion 10 is fixed in the second cooling passage 392. One end of the cool driving portion 80 is abutted with the cooling inlet 45. A peripheral side of the cool driving portion 80 is abutted with the first cooling passage 391 and the second cooling passage 392. The ends of the first cooling passage 391 and the second cooling passage 392 away from the cooling driving portion 80 are abutted with the first cooling outlet 46.

In this embodiment, the cooling bracket 39*a* is fixedly connected to the cool driving portion 80, and is provided with the first cooling passage 391 and the second cooling passage 392 that are abutted with the driving outlet 82. The first cooling passage 391 is separated from the second cooling passage 392. The heat removal assembly 70 is fixed in the first cooling passage 391, so as to use the cooling medium in the first cooling passage 391 to take away heat. The cold compressing portion 10 is fixed to the cooling bracket 39*a* and is opposite to the heat removal assembly 70, to receive the light emitted by the heat removal assembly 70, and emit the light. The heat conducting assembly is fixed to the cooling bracket 39*a*, one part of the heat conducting assembly is in contact with the cold compressing portion 10, and the other part of the heat conducting assembly is arranged in the second cooling passage 392, to absorb the heat of the cold compressing portion 10 and guide the heat to the second cooling passage 392. The cooling medium in the second cooling passage 392 takes away the heat.

Because the cooling bracket 39*a* defines the first cooling passage 391 and the second cooling passage 392, both the first cooling passage 391 and the second cooling passage 392 are abutted with the driving outlet 82 of the cool driving portion 80, and the heat removal assembly 70 is fixed in the first cooling passage 391, a part of the heat conducting assembly is in contact with the cold compressing portion 10, and the other part of the heat conducting assembly is arranged in the second cooling passage 392, so, the heat dissipation of the heat conducting assembly is separated from the heat dissipation of the heat removal assembly 70, which can effectively improve an overall cooling efficiency inside the depilator 100*a*.

In this embodiment, the cool driving portion 80 drives the external cooling medium to flow into the depilator 100*a*, so that the external cooling medium flows into the first cooling passage 391 and the second cooling passage 392, which facilitates the external cooling medium to take the heat of the heat removal assembly 70 and the heat conducting assembly away simultaneously. Specifically, the outside of the driving outlet 82 is snap-connected to the cooling bracket 39*a*, so as to realize the sealing and the abutting of the driving outlet 82 with the first cooling passage 391 and the second cooling passage 392, thereby reducing a resistance of external cooling medium entering into the first cooling passage 391 and the second cooling passage 392.

The cool driving portion 80 drives the external cooling medium to flow through a power device, so that the external cooling medium can effectively take away the heat in the depilator 100*a*. The driving outlet 82 is abutted the first cooling passage 391 and the second cooling passage 392, so that the cool driving portion 80 uses the power device to drive the external cooling medium in two cooling channels to cool the heat removal assembly 70 and the heat conducting assembly respectively. Thus, the internal structure of the depilator 100*a* is optimized, and the internal heat dissipation efficiency of the depilator 100*a* is increased.

In this embodiment, the cooling bracket 39*a* includes a bracket head 393. The cold compressing portion 10 is fixed to the bracket head 393 so that the cold compressing portion 10 contacts the skin of the user. One end of the hand-held portion 41 is firmly connected to the bracket head 393. The cooling bracket 39*a* is abutted with the driving outlet 82 at the opposite position or adjacent side of the bracket head 393. The first cooling passage 391 and the second cooling passage 392 are abutted side by side with the driving outlet 82. The first cooling passage 391 and the second cooling passage 392 are separated by a partition.

In this embodiment, the heat removal assembly 70 emits light toward the cold compressing portion 10. The heat of the heat removal assembly 70 can be taken away by the external cooling medium of the first cooling passage 391, and the external cooling medium of the first cooling passage 391 is directly obtained by the cooling driving portion 80 sucking the cooling medium of which external temperature is lowered, so as to achieve an effective reduction in the temperature of the heat removal assembly 70.

In this embodiment, the cold compressing portion 10 partially exposes the bracket head 393 so that the cold compressing portion 10 can contact the skin of the user. The cold compressing portion 10 is used to contact the skin of the user and emit light. The cold compressing portion 10 has a cold compressing surface 11. The cold compressing surface 11 is parallel to an outer end surface of the bracket head 393. The cold compressing portion 10 also has a heat conducting surface 12 that exposes the bracket head 393 and is arranged on the peripheral side of the cold compressing portion 10. The heat conducting surface 12 is attached to a part of the heat conducting assembly so that the heat of the cold compressing portion 10 is conducted from the heat conducting surface 12 to the heat conducting assembly, so that the cold compressing portion 10 achieves a cooling effect and its temperature reducing rate is accelerate.

Optionally, the cold compressing surface 11 is a flat surface, and the heat conducting surface 12 is a flat surface.

Optionally, the cold compressing surface 11 is an end surface of the cold compressing portion 10, and the heat conducting surface 12 is a side surface of the cold compressing portion 10.

In this embodiment, a part of the heat conducting assembly is fixed to the bracket head 393 and is in contact with the heat conducting surface 12 of the cold compressing portion 10, and the other part of the heat conducting assembly extends from a part of the cooling bracket 39*a* away from the bracket head 393, such that the external cooling medium in the second cooling passage 392 can take away the heat of the cold compressing portion 10, so as to reduce the temperature of the cold compressing portion 10 and reduce the burning sensation of light emitted by the cold compressing portion 10 on the skin of the user.

Furthermore, the heat conducting assembly includes the heat conducting plate 30a attached to the cold compressing portion 10, the first heat sink assembly 20a and the second heat sink assembly 20b attached to the heat conducting plate 30a. The heat conducting plate 30a is fixed on the cooling bracket 39a. The end of the heat conducting plate 30a away from the cold compressing portion 10 covers the second cooling passage 392. The first heat sink assembly 20a is accommodated in the second cooling passage 392 and is in contact with one part of the heat conducting plate 30a covering the second cooling passage 392. The second heat sink assembly 20b is fixed on the side of the heat conducting plate 30a away from the first heat sink assembly 20a. The second heat sink assembly 20b is adjacent to the cooling inlet 45 to increase the area of the heat conducting assembly contacting the external cooling medium, so as to increase the heat exchange rate between the heat conducting assembly and the external cooling medium, thereby increasing a cooling rate of the cold compressing portion10 to the heat conducting assembly.

In this embodiment, the heat conducting plate 30a is a flat plate. The heat conducting plate 30a adopts two plates to be laminated and sealed, and a heat conducting net is arranged between the two plates. A heat conducting medium is also arranged between the two plates of the heat conducting plate 30a, and the heat conducting net is fully contacted with the heat conducting medium, so that the contact area between the heat conducting medium and the heat conducting net is increased. The heat conducting medium can quickly absorb the heat absorbed by the heat conducting plate 30a from the cold compressing portion 10, and quickly conduct the heat to the first heat sink assembly 20a, so that the heat can be dissipated by the first heat sink assembly 20a. The heat conducting plate 30a is a short heat conducting plate 30a, that is, the distance between the heat conducting plate 30a contacting the cold compressing portion 10 and the heat conducting plate 30a contacting the first heat sink assembly 20a is relatively short, so that the heat conducting plate 30a can conduct heat to the first heat sink assembly 20a more quickly, which facilitates the first heat sink assembly 20a to take away the heat quickly by using the cooling medium in the second cooling passage 392, so as to quickly cool down the cold compressing portion 10, and improve the cooling rate of the depilator 100a.

Optionally, both plates of the heat conducting plate 30a are copper plates. The heat conducting net is a copper net with a capillary structure, so that the contact area between the heat conducting medium and the two plates is enlarged and more even, and the heat conducting efficiency of the heat conducting plate 30a is improved.

Optionally, a vacuum sealed cavity is arranged between the two plates of the heat conducting plate 30a, and the heat conducting medium and the heat conducting net are received in the sealed cavity.

Optionally, the heat conducting medium of the heat conducting plate 30a is a cooling liquid, preferably water quality.

Optionally, the edges of the two plates of the heat conducting plate 30a are sealed and pressed together, so that the heat conducting plate 30a has a stable structure and prevents the heat conducting plate 30a from getting heat inside.

In this embodiment, the first heat sink assembly 20a includes a plurality of side-by-side heat sinks 201a attached to the heat conducting plate 30a. By using the heat sinks 201a to contact the heat conducting plate 30a, the contact area between the first heat sink assembly 20a and the heat conducting plate 30a is increased. By using the heat conducting plate 30a to seal the second cooling passage 392, the external cooling medium in the second cooling passage 392 can be avoided to be leaked. The heat sinks 201a can quickly absorb the heat of the heat conducting plate 30a. There is a cooling medium flow space between the plurality of heat sinks 201a, a cooling medium flow direction between the plurality of heat sinks 201a is consistent with an extension direction of the second cooling passage 392, so that the cooling medium in the second cooling passage 392 can quickly flow through the flow space between the plurality of heat sinks 201a, so that the cooling medium in the second cooling passage 392 can quickly absorb the heat of the heat sinks 201a and take the heat away, thereby realizing effective heat dissipation of the heat conducting plate 30a. The second heat sink assembly 20b has substantially the same structure as the first heat sink assembly 20a, and will not be repeated here.

Furthermore, the cooling bracket 39a includes a bottom shell 394a and a top shell 395a which is covered with the bottom shell 394a. The heat conducting plate 30a is fixed to one side of the top shell 395a away from the bottom shell 394a. A part of the cold compressing portion 10 is fixed to between the bottom shell 394a and the top shell 395a, the other part of the cold compressing portion 10 passes through the top shell 395a to contact the heat conducting plate 30a. The first cooling passage 391 is formed between the bottom shell 394a and the top shell 395a. The second cooling passage 392 is formed between the bottom shell 394a and the heat conducting plate 30a.

In this embodiment, the top shell 395a defines a gap 3951a interconnecting with the second cooling passage 392. The heat conducting plate 30a seals and covers the gap 3951a, so that the heat conducting assembly seals the gap 3951a, to facilitate a part of the heat conducting assembly to extend into the second cooling passage 392. The heat sinks 201a are completely received in the second cooling passage 392. An accommodating groove 396 interconnecting with the first cooling passage 391 is also defined between the top shell 395a and the bottom shell 394a. The cold compressing portion 10 is fixed to the accommodating groove 396 so that the light from the heat removal assembly 70 can irradiate the cold compressing portion 10. The heat conducting surface 12 (see FIG. 6) extends out the accommodating groove 396 from the top shell 395a. The cold compressing surface 11 protrudes from the end surface of the bracket head 393 out of the accommodating groove 396 so that the cold compressing surface 11 contacts the skin of the user. The top shell 395a effectively supports the heat conducting plate 30a, and the size of the heat conducting plate 30a is equivalent to the size of the top shell 395a, making the internal structure of the depilator 100a more compact, which can effectively reduce the volume of the depilator 100a, to facilitate carrying.

In this embodiment, the cooling bracket 39a defines a first transfer port 66 that interconnects with the first cooling passage 391 and the second cooling passage 392 and is away from the driving outlet 82. The first transfer port 66 is disposed between the top shell 395a and the bottom shell 394a. The first transfer port 66 is arranged on one side wall of the cooling support 39a adjacent to the cold compressing portion 10 and is away from the driving inlet 81.

Specifically, half of the first transfer port 66 is defined on the top shell 395a, and the other half of the first transfer port 66 is defined on the bottom shell 394a. The side wall of the cooling bracket 39a opposite to the cold compressing portion 10 defines the first transfer port 66. The driving outlet 82 is abutted with the other side wall of the cooling bracket 39a. The cooling bracket 39a defines a second transfer port 65 on the other side wall adjacent to the cold compressing portion 10. The driving outlet 82 of the shell 83 is abutted with the second transfer port 65. The first cooling passage 391 and the second cooling passage 392 are formed between the second transfer port 65 and the first transfer port 66. The cool driving portion 80 is disposed on one side of the cooling bracket 39a, so that the driving outlet 82 blows the cooling medium to the second transfer port 65 and discharges the cooling medium from the first transfer port 66. The inner cooling medium of the cooling bracket 39a is blown in from one side of the cooling bracket 39a and blown out from the other side of the cooling bracket 39a, so that the flow rate of the inner cooling medium from the first cooling passage 391 to the second cooling passage 392 increases, thereby increasing the heat dissipation efficiency.

In this embodiment, the cool driving portion 80, the cooling bracket 39a, and the heat conducting assembly are all fixed in the receiving space 411. The first cooling outlet 46 is abutted with the first transfer port 66 so that the cooling medium entering the cooling bracket 39a can be quickly discharged from the first cooling outlet 46, thereby preventing the cooling medium that has absorbed from returning back to the inside of the cooling bracket 39a. Of course, there may also be a certain distance between the first cooling outlet 46 and the first transfer port 66, so that the cooling medium discharged from the first cooling outlet 46 can be partially discharged out of the housing 40 from the first transfer port 66, and partially enter the housing 40 to continue to cool down other components in the housing 40.

Furthermore, the lamp tube holder 73 is fixed in the cooling bracket 39a and is close to the cold compressing portion 10. The lamp tube 71 and the reflecting plate 72 are fixed on the lamp tube holder 73. The reflecting plate 72 is located on one side of the lamp tube 71 away from the cold compressing portion 10, and the reflecting plate 72 collects the light from the lamp tube 71 on the cold compressing portion 10.

In this embodiment, the lamp tube 71, the reflecting plate 72, and the lamp tube holder 73 are all located in the first cooling passage 391. The lamp tube 71, the reflecting plate 72 and the lamp tube holder 73 are all fixed a part of in the first cooling passage 391 adjacent to the cold compressing portion 10, so as to reduce a light path of the lamp tube 71 and prevent the heat of the light from being conducted to more devices, and reduce heat accumulation in the first cooling passage 391. More specifically, the lamp tube holder 73 is fixed to between the bottom shell 394a and the top shell 395a, so that the lamp tube holder 73 and the cooling bracket 39a are structurally stable. The lamp tube 71, the reflecting plate 72 and the lamp tube holder 73 are adjacent to the first transfer port 66, so that the cooling medium can immediately discharge the heat from the first transfer port 66 after absorbing the heat of the lamp tube 71, the reflecting plate 72 and the lamp tube holder 73, effectively reducing the heat of the lamp tube 71, the reflecting plate 72 and the lamp tube holder 73. The reflecting plate 72 condenses and reflects the light of the lamp tube 71 to increase the light concentration of the cold compressing portion 10. The two ends of the reflecting plate 72 have openings, so that the cooling medium flows through one opening of the reflecting plate 72 to the other opening, and the external cooling medium contacts the peripheral side of the lamp tube 71 to form convection and effectively cool the lamp tube 71. The two openings of the reflecting plate 72 are respectively adjacent to the first transfer port 66 and the second transfer port 65, so that the cooling medium in the first cooling passage 391 quickly flows through the inner side of the reflecting plate 72 to improve the heat dissipation efficiency of the lamp tube 71.

It can be understood that the heat inside the fuselage of the current traditional depilator 100a is large, which is likely to cause dangers such as short circuit, burnout, explosion and the like to the internal components of the depilator 100a. However, the heat conducting plate 30a of the present disclosure uses the cooling medium in the second cooling passage 392 to effectively cool down the cold compressing portion 10. The heat removal assembly 70 uses the cooling medium of the first cooling passage 391 to effectively dissipate heat, so that the cold compressing portion 10 can effectively cold compress the skin of the user, with high comfort and no skin damage. The temperature of the heat removal assembly 70 is effectively reduced, and the cooling medium can also be used to cool down other internal components of the depilator 100a, so that the body of the depilator 100a is cooled as a whole, and the internal temperature of the depilator 100a is prevented from being too high and causing harm. Specifically, the heating deices 50 of the depilator 100a of the present disclosure generates heat when it is working, the cool driving portion 80 can also drive the external cooling medium to flow into the housing 40 to contact the heating deices 50, and use the external cooling medium to take away the heat of the heating deices 50, to achieve rapid cooling of the internal components and the heating devices 50 of the depilator 100a, avoid excessive heat in the receiving space 411 of the depilator 100a, and prevent the heat removal assembly 70 and the heating deice 50 from danger situations such as short-circuiting, burning, and explosions.

In this embodiment, the heating deices 50 are arranged inside of the housing 40, and is optionally arranged on one part of the cooling bracket 39a away from the cold compressing portion 10. The heating deices 50 are set on the side of the heat removal assembly 70 away from the cold compressing portion 10, that is, the side of the heat removal assembly 70 away from the human skin. This design expands the contact range of the external cooling medium that is allowed in the receiving space 411 to reach the overall cooling effect inside of the housing 40.

Compared with the prior art, the depilator 100a of the third embodiment of the present disclosure has at least the following advantages:

1. The cooling bracket 39a includes the first cooling passage 391 and the second cooling passage 392. Both the first cooling passage 391 and the second cooling passage 392 are abutted with the driving outlet 82 of the cool driving portion 80, and are fixed to the first cooling passage 391 by the heat removal assembly 70. A part of the heat conducting assembly is in contact with the cold compressing portion 10, and the other part of the heat conducting assembly is disposed in the second cooling passage 392, so that the heat dissipation of the heat conducting assembly is separated from the heat dissipation of the heat removal assembly 70, thereby effectively improving the overall cooling efficiency inside the depilator 100a.

2. The depilator 100a adopts the heat conducting plate 30a with a composite structure, and the heat conducting plate 30a uses two laminated plates and a heat conducting medium and a heat conducting net sealed between the two plates to increase the heat conducting efficiency of the heat conducting plate 30a. The heat conducting plate 30a absorbs the heat of the cold compressing portion 10, so that the heat of the cold compressing portion 10 is rapidly reduced. The heat conducting plate 30a is made of copper material, so that the heat conducting efficiency of the heat conducting plate 30a is increased, and the heat conducting plate 30a can effectively absorb heat and dissipate heat effectively and quickly.

3. In the past, only a sealed cavity was used to separately protect the cooling member 18 of the cold compressing portion 10 to ventilate it. The heat removal assembly 70, which also generates heat, has not been considered, especially when used for a long time, the heat of the heat removal assembly 70 will very high, so the cooling effect is not complete. The depilator 100a of the present disclosure uses the cold compressing portion 10 and the heat removal assembly 70 to be simultaneously cooled respectively, so that the overall cooling effect is greatly improved, and the overall temperature in the body of the depilator 100a is effectively reduced.

4. The cooling inlet 45 is arranged on one side of the head portion 42, so that the cooling medium can be discharged quickly, and the heat dissipation efficiency of the cold compressing portion 10 and the heat removal assembly 70 is improved. The first cooling outlet 46 is arranged at a part of the housing 40 adjacent to the heat removal assembly 70 and the cold compressing portion 10, and facilitates to discharge out the heat from the heat removal assembly 70 and the heat conducting assembly, thereby increasing heat dissipation efficiency. The second cooling outlet 47 is arranged at the tail end of the depilator 100a away from the cold compressing portion 10, so that the flow path of the cooling medium in the depilator 100a is lengthened before being discharged, and the heat flowing through the heating deices 50 is discharged and the heat of the heating deice 50 is reduced.

5. The cold compressing member 19 is exposed from the head portion 42 of the housing 40 and actually contacts the human skin, so that the user can feel the cold compressing effect of the cold compressing member 19 while using the depilator 100a to remove hair, thereby reducing the strong pain sensation caused by the heat generated by the heat removal assembly 70.

6. The cold compressing member 19 is made of crystal material, which can be made of sapphire. Sapphire has strong thermal conductivity, which can reduce the heat of the light emitted by the depilator 100a while maintaining the light transmittance.

7. The cooling member 18 can be a TEC semiconductor refrigeration chip, which can effectively improve the cooling effect of the depilator 100a.

8. The heat conduction plate 30a is a VC uniform temperature plate, and its uniformity effect is better than that of heat pipes or metal substrate radiators, which can make the surface temperature more uniform (reduce hot spots). Secondly, the use of the VC uniform temperature plate allows the heat source to directly contact the VC uniform temperature plate, thereby reducing thermal resistance.

The above are the implementation modes of the embodiments of the present disclosure. It should be pointed out that for those of ordinary skill in the art, several improvements and modifications can be made without departing from the principle of the embodiments of the present disclosure, and these improvements and modifications are also treated as the protection scope of the present disclosure.

What is claimed is:

1. A depilator, wherein the depilator comprises a cold compressing portion, a heat removal assembly, a heat sink assembly and a heat conducting plate; the heat conducting plate comprises a main heat absorbing portion and a heat outputting portion; the main heat absorbing portion is in contact with the cold compressing portion, to absorb heat of the cold compressing portion; the heat outputting portion is in contact with the heat sink assembly, to conduct the heat to the heat sink assembly; the depilator defines a cooling channel; the depilator comprises a housing; the housing defines at least one cooling inlet and at least one cooling outlet; the cooling channel is formed between the at least one cooling inlet and the at least one cooling outlet; the heat of the heat sink assembly is dissipated through the cooling channel and the at least one cooling outlet;

the heat removal assembly comprises a lamp tube for emitting light to the cold compressing portion;
the cooling channel comprises a first cooling passage and a second cooling passage;
wherein, at least part of the lamp tube is disposed in the first cooling passage, and at least part of the heat sink assembly is disposed in the second cooling passage;
wherein the depilator further comprises a plurality of heating devices; the heat conducting plate also comprises a plurality of secondary heat absorbing portions; the secondary heat absorbing portions are in contact with at least part of the heating devices, to absorb heat of the heating devices.

2. The depilator according to claim 1, wherein the heat conducting plate is VC uniform temperature plate.

3. The depilator according to claim 1, wherein the heating devices and the cold compressing portion are in contact with a same surface of the heat conducting plate; the cold compressing portion and the heat sink assembly are respectively in contact with two opposite surfaces of the heat conducting plate.

4. The depilator according to claim 1, wherein the heat conducting plate covers the cold compressing portion, the heating devices, and the heat sink assembly.

5. The depilator according to claim 1, wherein external cooling medium is introduced into the cooling channel; the heat outputting portion, the plurality of secondary heat absorbing portions, the heating devices and the heat sink assembly are all located in the cooling channel.

6. The depilator according to claim 1, wherein the cold compressing portion is isolated from the cooling channel.

7. The depilator according to claim 1, wherein the depilator comprises a cool driving portion, and the cool driving portion is configured to drive external cooling medium in the cooling channel to flow.

8. The depilator according to claim 7, wherein the cool driving portion defines at least one driving inlet and at least one driving outlet; the external cooling medium flows through the driving inlet to the driving outlet; the heating devices are close to the driving outlet; the heat outputting portion of the heat conducting plate and the heat sink assembly are both close to the driving inlet.

9. The depilator according to claim 1, wherein the cold compressing portion comprises a cold compressing member; the cold compressing member is configured to contact a skin of a user and cold compress.

10. The depilator according to claim 9, wherein a material of the cold compressing member is sapphire crystal.

11. The depilator according to claim 9, wherein the cold compressing portion further comprises a cooling member for cooling the cold compressing member, wherein the cooling member comprises a cooling surface that is attached to the cold compressing member and a heat conducting surface opposite to the cooling surface; the main heat absorbing portion is attached to the heat conducting surface, to absorb the heat from the heat conducting surface.

12. The depilator according to claim 1, wherein the depilator also comprises a cooling bracket; the first cooling passage and the second cooling passage are defined by the cooling bracket; the first cooling passage and the second cooling passage are formed as part of the cooling channel; an end of the heat conducting plate away from the cold compressing portion covers the second cooling passage; the heat sink assembly is received in the second cooling passage.

13. The depilator according to claim 12, wherein the cooling bracket comprises a bottom shell and a top shell covering the bottom shell; the heat conducting plate is fixed to one side of the top shell away from the bottom shell; a part of the cold compressing portion is fixed between the bottom shell and the top shell, and the other part of the cold compressing portion passes through the top shell to contact the heat conducting plate; the first cooling passage is formed between the bottom shell and the top shell; the second cooling passage is formed between the bottom shell and the heat conducting plate.

14. The depilator according to claim 13, wherein the cooling bracket comprises a bracket head; the cold compressing portion is fixed to the bracket head; the cold compressing portion has a cold compressing surface and a heat conducting surface on a peripheral side of the cold compressing portion; the heat conducting surface is attached to a part of the heat conducting plate so that the heat of the cold compressing portion is conducted from the heat conducting surface to the heat conducting plate.

15. The depilator according to claim 14, wherein an accommodating groove interconnecting with the first cooling passage is further defined between the top shell and the bottom shell; the cold compressing portion is fixed in the accommodating groove, so that light of the heat removal assembly is able to irradiate to the cold compressing portion; the heat conducting surface extends out of the accommodating groove from the top shell; the cold compressing surface extends the accommodating groove from an end surface of the bracket head, so that the cold compressing surface is in contact with a skin of a user.

16. The depilator according to claim 12, wherein the heat sink assembly is a first heat sink assembly, the heat sink assembly further comprises a second heat sink assembly; the second heat sink assembly is fixed on one side of the heat conducting plate away from the first heat sink assembly; and the second heat sink assembly is adjacent to the cooling inlet.

17. The depilator according to claim 12, wherein the depilator further comprises a cool driving portion; the cool driving portion is fixed to one side of the heat removal assembly away from the cold compressing portion and is fixedly connected to the cooling bracket, for driving external cooling medium to flow through a part of the heat conducting plate and the heat sink assembly away from the cold compressing portion, so that the heat of the heat conducting plate and the heat sink assembly is taken away by the external cooling medium.

18. The depilator according to claim 17, wherein the cool driving portion defines at least one driving inlet and at least one driving outlet; the driving outlet is snap-connected to the cooling bracket so that the driving outlet is abutted with the first cooling passage and the second cooling passage; the external cooling medium flows through the driving inlet, the driving outlet, and further flows out through the first cooling passage or the second cooling passage.

19. The depilator according to claim 1, wherein external cooling medium is introduced into the cooling channel; wherein, a part of the external cooling medium flows to the lamp tube, and another part of the external cooling medium flows to at least part of the heat sink assembly.

20. The depilator according to claim 1, wherein external cooling medium is introduced into the cooling channel; wherein, a part of the external cooling medium flows into the first cooling passage, and another part of the external cooling medium flows into the second cooling passage.

21. The depilator according to claim 1, wherein the at least one cooling outlet comprises two cooling outlets; wherein,
 external cooling medium is introduced into the cooling channel; wherein,
 a part of the external cooling medium flows into the first cooling passage, passes through the lamp tube, and is discharged through one of the two cooling outlets; and
 another part of the external cooling medium flows into the second cooling passage, and is discharged through the other one of the two cooling outlets.

22. The depilator according to claim 21, wherein the at least one cooling outlet further comprises another cooling outlet; wherein,
 the external cooling medium is discharged through, in addition to the two cooling outlets, the another cooling outlet.

23. The depilator according to claim 1, wherein the at least one cooling outlet comprises:
 a first cooling outlet;
 a second cooling outlet; and
 a third cooling outlet; wherein,
 external cooling medium is introduced into the cooling channel; wherein,
 a part of the external cooling medium flows into the first cooling passage, passes through the lamp tube, and is discharged through the first cooling outlet and the second cooling outlet; and
 another part of the external cooling medium flows into the second cooling passage, and is discharged through the third cooling outlet.

* * * * *